(12) United States Patent
Piston et al.

(10) Patent No.: US 7,351,537 B2
(45) Date of Patent: Apr. 1, 2008

(54) VARIANTS OF CYAN FLUORESCENT PROTEIN WITH IMPROVED FLUORESCENT PROPERTIES

(75) Inventors: David Piston, Nashville, TN (US); Mark Rizzo, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 10/948,846

(22) Filed: Sep. 23, 2004

(65) Prior Publication Data

US 2005/0089908 A1 Apr. 28, 2005

Related U.S. Application Data

(60) Provisional application No. 60/505,299, filed on Sep. 23, 2003.

(51) Int. Cl.
| | |
|---|---|
| C12Q 1/68 | (2006.01) |
| C12P 1/00 | (2006.01) |
| C12N 5/00 | (2006.01) |
| C07H 21/04 | (2006.01) |
| C07K 14/00 | (2006.01) |

(52) U.S. Cl. .......................... 435/6; 435/41; 435/69.1; 435/325; 435/410; 536/23.1; 530/350

(58) Field of Classification Search ................. 530/350
See application file for complete search history.

(56) References Cited

OTHER PUBLICATIONS

Chiu et al., "Ras signalling on the endoplasmic reticulum and the Golgi," *Nat Cell Biol*, 4(5):343-350, 2002.
Cubitt et al., "Understanding structure-function relationships in the Aequorea victoria green fluorescent protein," *Methods Cell Biol*, 58:19-30, 1999.
Greisbeck et al., "Reducing the environmental sensitivity of yellow fluorescent protein," *J. Biol. Chem.*, 276(31):29188-29194, 2001.
Heim and Tsien, "Engineering green fluorescent protein for improved brightness longer wavelengths and fluorescence resonance energy transfer," *Curr Biol*, 6(2):178-182, 1996.
Hyun Bae et al., "Expansion of the genetic code enables design of a novel 'gold' class of green fluorescent proteins," *J. Mol. Biol.*, 328:1071-1081, 2003.
Karasawa et al., "Cyan-emitting and orange-emitting fluorescent proteins as a donor/acceptor pair for fluorescence resonance enerty transfer," *Biochem J.*, 381:307-312, 2004.
Miyawaki et al., "Fluorescent indicators for Ca$^{2+}$ based on green fluorescent proteins and calmodulin," *Nature*, 388:882-887, 1997.
Nagai et al., "A variant of yellow fluorescent protein with fast and efficient maturation for cell-biological applications," *Nature Biotechnology*, 20(1):87-90, 2002.
Ormo et al., "Crystal structure of the aequorea victoria green fluorescent protein," *Science*, 273(5280):1391-1395, 1996.
Patterson et al., "Fluorescent protein spectra," *J Cell Sci*, 114:837-838, 2001.
Patterson et al., "Förster distances between green fluorescent protein pairs," *Anal Biochem*, 284(2):438-440, 2000.
Rizzo et al., "A functional link between glucokinase binding to insulin granules and conformational alterations in response to glucose and insulin," *J. Biol. Chem.*, 277(37):34168-34175, 2002.
Rizzo et al., "An improved cyan fluorescent protein variant useful for FRET," *Nat Biotechnol*, 22(4):445-449, 2004.
Sawano and Miyawaki, "Directed evolution of green fluorescent protein by a new versatile PCR strategy for site-directed and semi-random mutagenesis," *Nucleic Acids Research*, 28(16):e78, 2000.
Sekar and Periasamy, "Fluorescent resonance energy transfer (FRET) microscopy imaging of live cell protein localizations," *J. Cell Biol*, 160(5):629-633, 2003.
Shagin et al., "GFP-like proteins as ubiquitous metazoan superfamily: evolution of functional features and structural complexity," *Mol Biol Evol*, 21(5):841-850, 2004.
Swedlow et al., "Measuring tubulin content in Toxoplasma gondii: a comparison of laser-scanning confocal and wide-field fluorescence microscopy," *Proc. Natl. Acad. Sci.*, USA, 99:2014-2019, 2002.
Ting et al., "Genetically encoded fluorescent reporters of protein tyrosine kinase activities in living cells," *Proc. Natl. Acad. Sci.*, USA, 98:15003-15008, 2001.
Tramier et al., "Picosecond-hetero-FRET microscopy to probe protein-protein interactions in live cells," *Biophysical Journal*, 83:3570-3577, 2002.
Truong et al., "FRET-based in vivo Ca2+ imaging by a new calmodulin-GFP fusion molecule," *Nat Struct Biol*, 8:1069-1073, 2001.
Tsien, "The green fluorescent protein," *Ann Rev Biochem*, 67:509-544, 1998.
Vanderklish et al., "Marking synaptic activity in dendritic spines with calpain substrate exhibiting fluorescence resonance energy transfer," *Proc. Natl. Acad. Sci.*, USA, 97:2253-2258, 2000.
Zacharias et al., "Partitioning of lipid-modified monomeric GFPs into membrane microdomains of live cells," *Science*, 296:913-916, 2002.
Zhang et al., "Genetically encoded reporters of protein kinase A activity reveal impact of substrate tethering," *Proc. Natl. Acad. Sci.*, USA, 98:14997-15002, 2001.

*Primary Examiner*—Maryam Monshipouri
*Assistant Examiner*—Marsha Tsay
(74) *Attorney, Agent, or Firm*—Fulbright & Jaworski, LLP

(57) ABSTRACT

The present invention provide optimized cyan fluorescent protein (oCFP) variants. In particular, the variants exhibit increase quantum yield of fluorescence and a single component fluorescence lifetime.

12 Claims, 4 Drawing Sheets

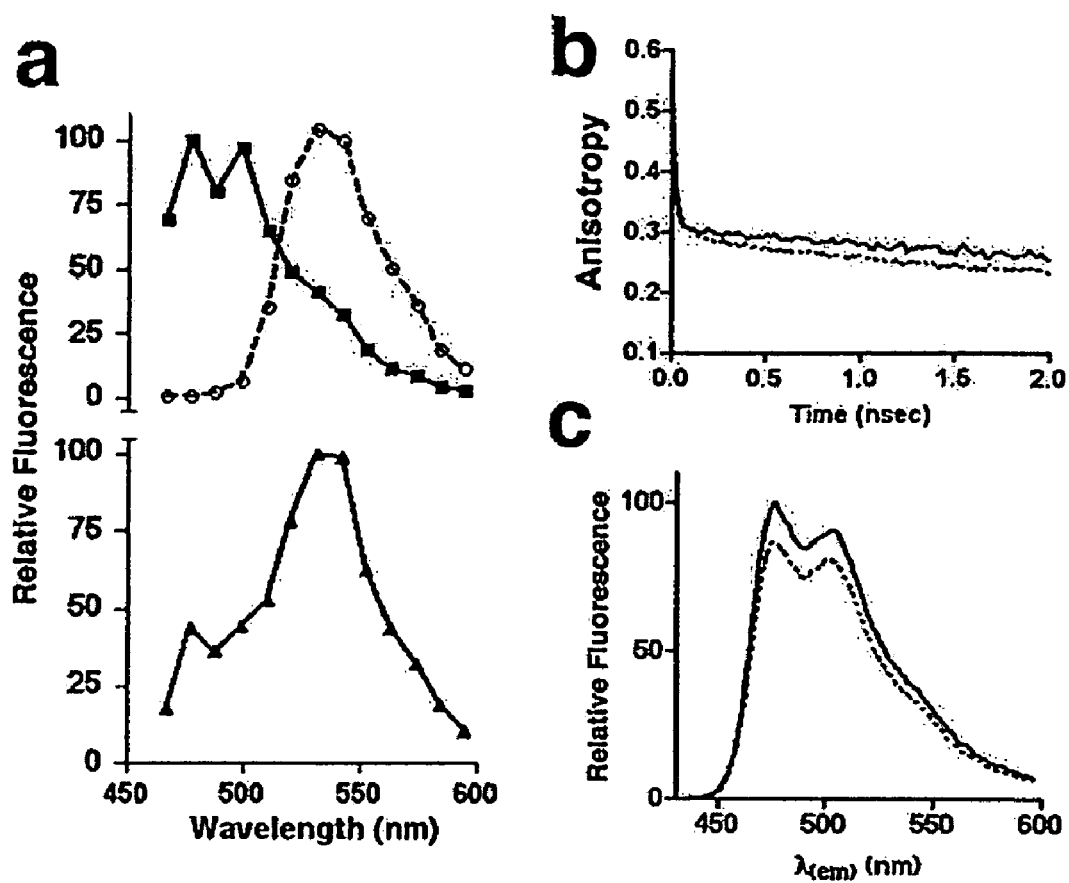
FIG. 1A-C

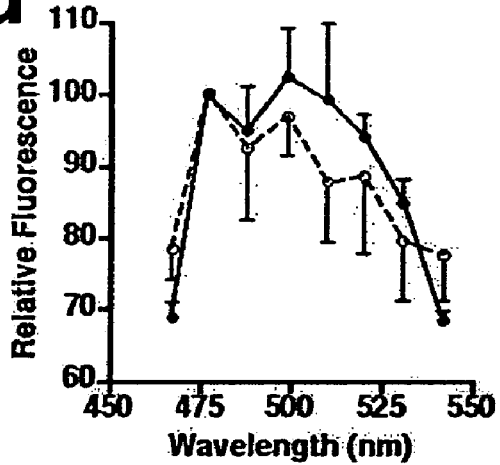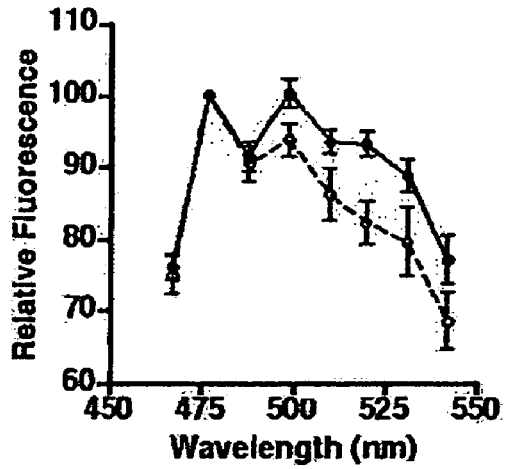
FIG. 2A-E

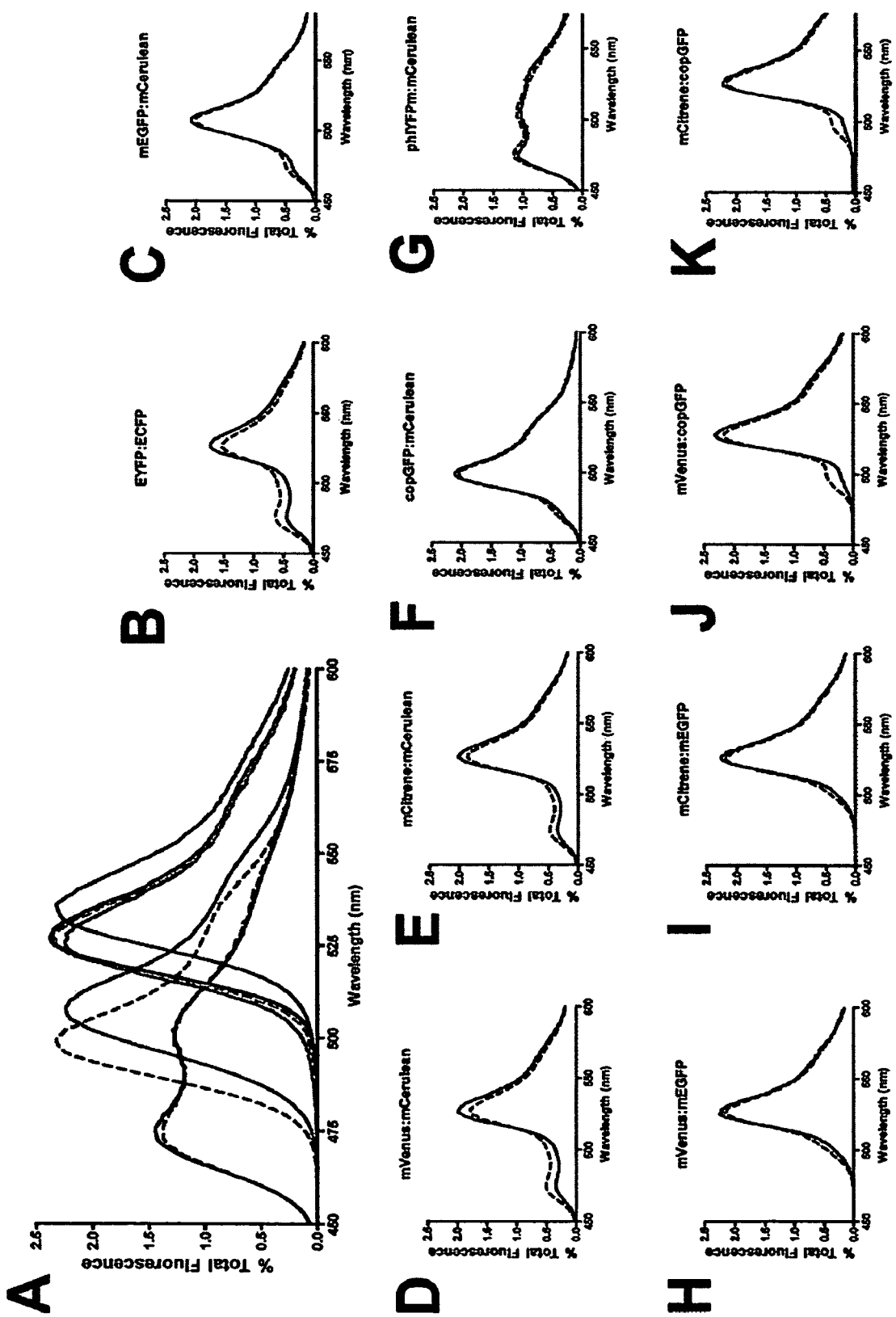
FIG 3A-K

VARIANTS OF CYAN FLUORESCENT PROTEIN WITH IMPROVED FLUORESCENT PROPERTIES

The present application claims benefit of priority to U.S. Provisional Application Ser. No. 60/505,299, filed Sep. 23, 2003, the entire contents of which are hereby incorporated by reference.

The government owns rights in the present invention pursuant to grants numbered DK53434 and DK60275 from the National Institutes of Health.

BACKGROUND OF THE INVENTION

1. Field of the Invention

The present invention relates generally to the fields of protein biochemistry and fluorescence resonance energy transfer. More specifically, the invention relates to the creation and use of novel cyan fluorescent protein variants with improved fluorescent characteristics.

2. Description of Related Art

The green fluorescent protein (GFP) from the jellyfish *Aequorea victoria* has provided a myriad of applications for biological systems (Tsien, 1998). Over the last several years, both random and semi-rational mutagenesis have produced GFP variants with new colors, improved folding properties, increased brightness, and altered pH-sensitivity. Through genetic manipulations, hundreds of proteins have been successfully fused to GFPs to allow monitoring of their expression and trafficking. When GFP or GFP-fusion proteins are heterologously expressed at a certain level, the intensity of the fluorescence depends on: (1) the ultimate brightness of GFP fluorophore, which is limited by the product of extinction coefficient and fluorescence quantum yield; (2) the maturation efficiency of newly-synthesized GFP polypeptides; and (3) the extent of quenching of GFP fluorophore by environmental factors.

Yellow fluorescent protein (YFP) is one of the most commonly used GFP variants and has the longest wavelength emission of all *Aequorea* GFP variants, and EYFP, containing the modification S65G, S72A and T203Y, is a common variant of YFP. The extinction coefficient and fluorescence quantum yield of most YFP variants are within 60,000 to 100,000 $M^{-1}$ $cm^{-1}$ and 0.6 to 0.8, respectively (Tsien, 1998). These values are almost comparable to those of common bright fluorophores, such as fluorescein and rhodamine. Therefore, the improvement of the ultimate brightness of YFP seems to have reached its limit.

Newly-synthesized GFP polypeptides need to mature properly before emitting fluorescence. The maturation involves two steps: first, the protein folding into a nearly native conformation, and then, cyclization of an internal tripeptide followed by oxidation. Some of the primary mutations that improve maturation of GFP have been identified (Tsien, 1998). For example, F64L, M153T, V163A, and S175G are common mutations introduced in many enhanced GFP variants. M153T and S175G are located on the surface of the β-barrel and are known to enhance the folding efficiency and the stability by reducing surface hydrophobicity and increasing the solubility of the protein.

Another study generated, using random mutagenesis on pericams (circularly-permuted GFPs engineered to sense $Ca^{2+}$), generated several mutations that improved the maturation without affecting the $Ca^{2+}$-sensitivity. Of particular interest was a mutation of Phe-46 to Leu, which greatly improved the formation of the chromophore at 37° C. The effect of the well-known folding mutation, F64L/M153T/V163A/T203Y, on EYFP was also studied along with that of F46L. The purified YFP variants exhibited exactly the same excitation and emission spectra. However, the F46L mutant also gave rise to about 20-fold increase in the fluorescence of cell pellet after 12 hr incubation. Both SEYFP and SEYFP-F46L refolded quickly with rate constants. Although F46L alone increased the speed and yield of recovery of EYFP and SEYFP, its effect was less potent than that of the common folding mutations. Thus, it was concluded that the mutations F64L/M153T/V163A/S175G were significantly effective in facilitating folding of YFP at 37° C. While SEYFP and SEYFP-F46L gave similar folding rate constants, the speed and yield of the renaturation from denatured/reduced protein at 37° C. was significantly improved by F46L. Interestingly, this improvement was not clearly observed when the studies were carried out at room temperature. Also, EYFP-F46L showed faster reoxidation than SEYFP at 37° C. This discussion illustrates that fluorescent variants can be engineered to, exhibit one or more beneficial properties selected from improved maturation speed, accelerated oxidation step, and decreased pH-sensitivity, each of which can lead to the enhancement of fluorescence development.

Thus, fluorescent proteins clearly are amenable to considerable engineering, and can be manipulated such that the variants exhibit additional beneficial properties not found in the natural molecules or existing variants. Therefore, there is an opportunity and need to create new and improved fluorescent proteins for a variety of uses.

SUMMARY OF THE INVENTION

Thus, in accordance with the present invention, optimized cyan fluorescent proteins (oCFPs) are provided. In one embodiment, the oCFP comprise an amino acid other than Y at position 145, such as alanine (Y145A), histidine (Y145H), proline (Y145P) or glycine (Y145G). The variant may further comprising insertion of valine at position 2, and/or substitution of serine at position 72 with alanine, and/or a non-hydrophobic residue at position 148, such as glutamic acid (H148E) or aspartic acid (H148D). In a particular embodiment, the variant is S72A/Y145A/H148D. Also provided are nucleic acids encoding each of the foregoing, and host cells comprising such nucleic acids.

In another embodiment, there is provided an optimized variant of cyan fluorescent protein comprising a non-hydrophobic residue at position 148, such as glutamic acid (H148E) or aspartic acid (H148D). The variant may further comprise insertion of valine at position 2, and/or substitution of serine at position 72 with alanine, and/or an amino acid other than Y at position 145, such as alanine (Y145A), histidine (Y145H), proline (Y145P) or glycine (Y145G). Also provided are nucleic acids encoding each of the foregoing, and host cells comprising such nucleic acids.

In yet another embodiment, there is provided a method of assessing fluorescence resonance energy transfer (FRET) comprising (a) bringing into FRET proximity an acceptor fluorescent protein (AFP) and an optimized variant of cyan fluorescent protein (oCFP), wherein the oCFP comprises an amino acid other than Y at position 145 and/or a non-hydrophobic residue at position 148; and (b) measuring FRET. The oCFP may comprise an amino acid other than Y at position 145 and histidine at position 148, and/or a non-hydrophobic residue at position 148 and Y at position 145, and/or an amino acid other than Y at position 145 and a non-hydrophobic residue at position 148. The oCFP may be attached to a first molecule and the AFP may be attached to a second molecule. The first and second molecules may be proteins and the oCFP and AFP may be fusion proteins with the first and second molecules, respectively. The method may further comprise contacting the oCFP and AFP with a candidate substance.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-C—Disadvantages of using ECFP in FRET studies. (FIG. 1A) The relative fluorescence emission spectra of a typical cell expressing a construct containing ECFP fused to mCit (bottom) as detected by spectral imaging. The top panel shows reference spectra for ECFP (solid line) and YFP (dotted line). (FIG. 1B) The time-resolved anisotropy decay of a purified ECFP:ECFP homodimer (dotted line) and monomeric ECFP (solid line)was measured using time-resolved spectroscopy and reveals homotransfer between the ECFP:ECFP homodimer (dotted line). (FIG. 1C) The steady-state fluorescence emission spectra of equal optical densities for purified ECFP:ECFP homodimer (dotted line) and monomeric ECFP (solid line).

FIGS. 2A-E—Comparison of Cerulean and ECFP. Cyan and yellow fluorescence was resolved by spectral imaging and linear unmixing in a representative COS-7 expressing either ECFP:mCit (FIG. 2A) or Cerulean:mCit (FIG. 2B). A histogram of the intensity distribution of pixels inside the cell for the cyan (in cyan) and yellow (in yellow) channels is shown on the right. (FIG. 2C) Yellow and cyan channels are shown from a βTC3 cell expressing the Cerulean GK biosensor before and after insulin stimulation (100 nM, 2 min). (FIG. 2D) Cellular intensities from a META stack were normalized to peak cyan fluorescence pre-(solid line) and post-(broken line) insulin stimulation of βTC3 cells (n=4) expressing either the ECFP GK biosensor (FIG. 2D) or the Cerulean GK biosensor (FIG. 2E). Error bars indicate standard error of the mean.

FIGS. 3A-K—(FIG. 3A) Steady-state emission spectra of individual fluorescent proteins normalized to total fluorescence: blue line, ECFP; dotted blue line, mCerulean; dotted green line, copGFP; green line, mEGFP; orange line, EYFP; black line, mVenus; dotted orange line, mCitrene; red line, phiYFP). (FIGS. 3B-K). Steady state emission spectra of coupled FRET pairings coupled by a linker of short linker of 10 amino acids (solid line) or a long linker of 44 amino acids (dotted line). (FIG. 3B) EYFP:ECFP; (FIG. 3C) mEGFP:mCerulean; (FIG. 3D) mVenus:mCerulean; (FIG. 3E) mCitrene:mCerulean; (FIG. 3F) copGFP:mCerulean; (FIG. 3G) phiYFP:mCerulean; (FIG. 3H) mVenus:mEGFP; (FIG. 3I) mCitrene:mEGFP; (FIG. 3J); mVenus:copGFP; (FIG. 3K) mCitrene:copGFP.

DESCRIPTION OF ILLUSTRATIVE EMBODIMENTS

I. The Present Invention

Figure 4:
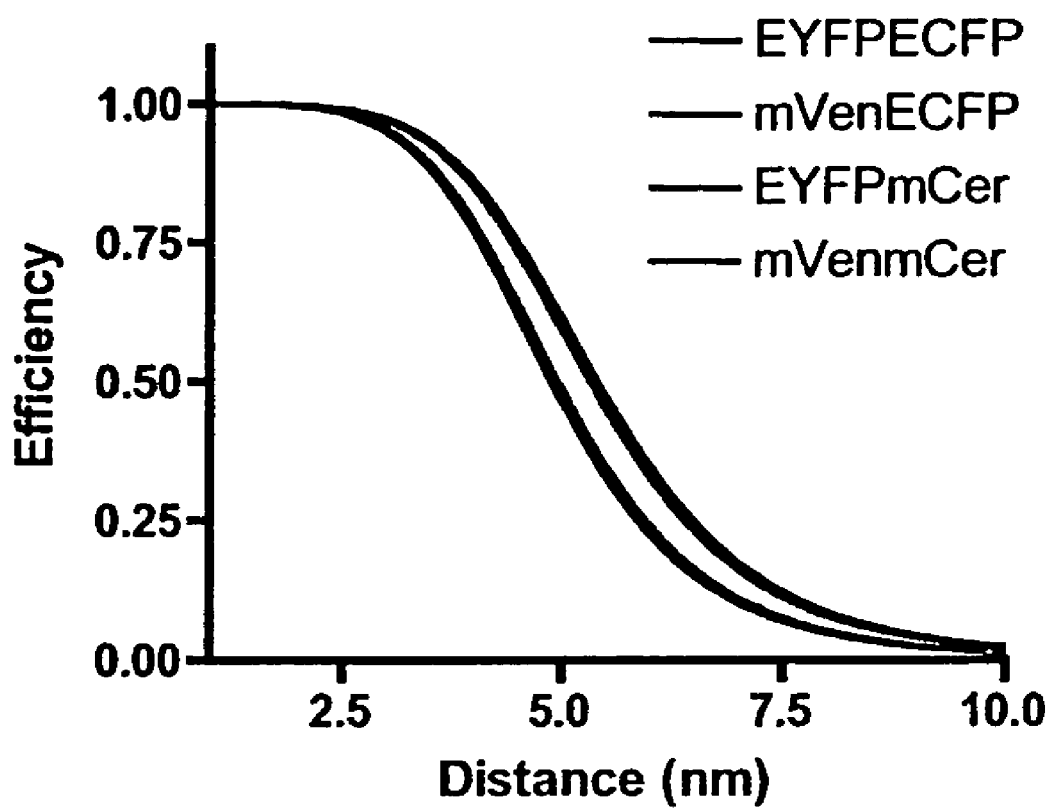
FIG. 4—Theoretical changes in FRET efficiency by exchange of EYFP and ECFP for optimized variants. Plot of $E=r_0^6/(r_0^6+r^6)$ where r is the distance separating the FRET pair and $r_0$ is the forster distance reported in Table 3 for the acceptor:donor pair: EYFP:ECFP (black), mVenus:ECFP (red), EYFP:mCerulean (green), and mVenus:mCerulean (blue).

As discussed above, fluorescent proteins derived from *Aequorea victoria* are powerful tools in examining the biological relationship of various molecules in cyto. In particular, it is common to fuse proteins to fluorescent proteins in order to track protein localization and function in living cells. Modification of the DNA sequence of the original green florescent protein (GFP) has produced several variants of fluorescent proteins with unique spectral and biochemical properties suitable for a wide variety of applications, including the cyan fluorescent protein (CFP) and yellow fluorescent protein (YFP). These two molecules exhibit special fluorescence excitation and emission properties that are suited to measurement of close molecular distances, in particular, by fluorescence resonance energy transfer, or "FRET." However, use of CFP in particular is limited by the fact that is exhibits a two different conformational states, leading to two-component fluorescence profile.

The present invention provides new optimized CFP (OCFP) variants that not only have improved overall brightness, but also exhibit single component fluorescence. For example, a first change is to replace the histidine at amino acid 148 with any hydrophilic amino acid, in particular, glutamic acid or aspartic acid. A second change is to substitute the tyrosine at amino acid 145 with any amino acid, in particular alanine, histidine, proline or glycine. In addition, previously identified alterations including a serine to alanine change at residue 72, and inserted valine between residues 1 and 2 may be utilized. These variants will find particular use in FRET studies, as discussed further below.

II. Fluorescent Proteins

The gene of the green fluorescent protein has been isolated and its sequence has also been determined (Prasher et al., 1992). There have also been numerous reports of amino acid sequences of other fluorescent proteins or their mutants, for example, as described in Tsin (1998) and the literature cited therein.

The term "cyan fluorescent protein (CFP)" as used herein is defined as any fluorescent protein with an absorption maximum between 420 and 460 nm, and a fluorescence maximum between 460 and 500 nm. These proteins have mainly been derived from the wild-type *Aequoria* GFP with a Y66W mutation, resulting in a primary excitation peak at ~434 nm with minor excitation maxima at ~452 nm, and a primary emission peak is ~477 nm with minor shoulder at ~505 nm (Heim et al., 1994). Other fluorescent proteins are termed "green fluorescent protein (GFP)", meaning proteins with absoption maxima between 480 and 500 nm and fluorescence maxima between 500 and 515 nm, and "yellow fluorescent protein (YFP)" meaning proteins with absoption maxima between 500 and 520 nm and fluorescence maxima between 515 and 535 nm.

A particular mutant of YFP, designated ECFP, contains mutations to optimize folding and expression in mamalian systems, including F64L, S65T, Y66W, N146I, M153T, V163A, H231L, with addition of Valine at position 2 (Heim and Tsien, 1996).

III. Peptides and Polypeptides

As discussed above, the present invention relates to optimized cyan fluorescent proteins (oCFP's). These proteins, being variants, are produced recombinantly. Thus, in certain embodiments, the present invention concerns proteinacious compositions comprising these oCFP's and subunits thereof. As used herein, "proteinaceous molecule," "proteinaceous composition," "proteinaceous compound," and or "proteinaceous material" generally refer to proteins of varying lengths but retain their fluorescent function. All the "proteinaceous" terms described above may be used interchangeably herein.

A number of changes may be introduced into a CFP to create an oCFP according to the present invention. Throughout the application, amino acid numbering for CFP conforms to a standard convention. A first change is to substitute the tyrosine at amino acid 145 with any amino acid, in particular alanine, histidine, proline or glycine. A second change is to replace the histidine at amino acid 148 any hydrophilic amino acid, in particular, aspartic acid, glutamic acid, glutamine or asparagine. In addition, previously identified alterations including a serine to alanine change at residue 72, and inserted valine between residues 1 and 2 may be utilized. The following table illustrates various potential combinations.

TABLE 1

SUMMARY OF POSSIBLE MUTATION COMBINATIONS

| Position 1–2 | Position 72 | Position 145 | Position 148 |
| --- | --- | --- | --- |
| — | Ser | Ala | Asp |
| — | Ser | His | Asp |
| — | Ser | Pro | Asp |
| — | Ser | Gly | Asp |
| — | Ser | Ala | Glu |
| — | Ser | His | Glu |
| — | Ser | Pro | Glu |
| — | Ser | Gly | Glu |
| — | Ala | Ala | Asp |
| — | Ala | His | Asp |
| — | Ala | Pro | Asp |
| — | Ala | Gly | Asp |
| — | Ala | Ala | Glu |
| — | Ala | His | Glu |
| — | Ala | Pro | Glu |
| — | Ala | Gly | Glu |
| Val | Ser | Ala | Asp |
| Val | Ser | His | Asp |
| Val | Ser | Pro | Asp |
| Val | Ser | Gly | Asp |
| Val | Ser | Ala | Glu |
| Val | Ser | His | Glu |
| Val | Ser | Pro | Glu |
| Val | Ser | Gly | Glu |
| Val | Ala | Ala | Asp |

TABLE 1-continued

SUMMARY OF POSSIBLE MUTATION COMBINATIONS

| Position 1–2 | Position 72 | Position 145 | Position 148 |
| --- | --- | --- | --- |
| Val | Ala | His | Asp |
| Val | Ala | Pro | Asp |
| Val | Ala | Gly | Asp |
| Val | Ala | Ala | Glu |
| Val | Ala | His | Glu |
| Val | Ala | Pro | Glu |
| Val | Ala | Gly | Glu |

1. Fusion Proteins

A fused fluorescent protein can be constructed by fusing the oCFP of the present invention with another protein. The kinds of "another protein" to be fused with the fluorescent protein of the present invention are not particularly limited. The methods for obtaining the fused fluorescent protein of the present invention are not limited. There may be used any of a chemically synthesized protein fusion, or a recombinant protein produced by a gene recombination technique.

In the case of producing a recombinant protein, it is necessary to obtain the DNA encoding the protein. By utilizing the information of the amino acid sequences shown in SEQ ID NO: 1 and the nucleotide sequences shown in SEQ ID NO: 2 of the sequence list herein, suitable primers can be designed, and by using those to perform PCR™ using a cDNA clone of various known fluorescent proteins as described above as a template, DNA fragments which is necessary for constructing DNA encoding the fluorescent protein of the present invention can be prepared. Further, DNA fragment encoding a protein to be fused is also obtained in the same manner.

Then, DNA encoding the desired fused fluorescent protein can be obtained by ligating those DNA fragments in order by means of a gene recombination technique. A fused fluorescent protein of the present invention can be produced by introducing this DNA into a suitable expression system.

By expressing the fused fluorescent protein obtained by fusing the fluorescent protein of the present invention with another protein (referred to as "protein X") as mentioned above in cells and monitoring the emitted fluorescence, the localization and dynamic situation of protein X in the cell can be analyzed. Thus, by observing a cell which was transformed or transfected with DNA encoding the fused fluorescent protein of the present invention by means of a fluorescent microscope, the localization and dynamic situation of protein X in the cell can be visualized and analyzed.

For example, by using a protein which is specific for intercellular organelles as protein X, distribution and movement of nucleus, mitochondrion, endoplasmic reticulum, secretory vesicles, peroxisome and the like can be observed. Moreover, since axon and dendroid axon of nerve cells show very complicated change of running direction in developing individuals, dynamic analysis can be carried out by labeling such sites with a fluorescence. Various targeting sequences are commercially available, such as DsRed2 subcellular localization vectors from Clontech, which facilitate nuclear, mitochondrial, peroxisomal and ER targeting.

2. Protein Purification

It may be desirable to purify proteins in accordance with the present invention. Protein purification techniques are well known to those of skill in the art. These techniques involve, at one level, the crude fractionation of the cellular milieu to polypeptide and non-polypeptide fractions. Such methods may include physical disruption followed by centrifugation, solvent extraction, salting-out (e.g., by ammonium sulfate or the like), desalting, precipitation, etc. Having thus separated generally the polypeptide from other molecules, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

The term "purified protein" as used herein is intended to refer to a proteinaceous composition, isolated from other components, wherein the protein or peptide is purified to any degree relative to its naturally-obtainable state. A purified protein or peptide therefore also refers to a protein or peptide, free from the environment in which it may naturally occur. Generally, "purified" will refer to a protein composition that has been subjected to fractionation to remove various other components, and which composition substantially retains its expressed biological activity. Where the term "substantially purified" is used, this designation will refer to a composition in which the protein forms the major component of the composition, such as constituting about 50%, about 60%, about 70%, about 80%, about 90%, about 95% or more of the proteins in the composition.

Various methods for quantifying the degree of purification of the protein will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein.

There is no general requirement that the protein always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

It may be necessary, following purification, to refold and reoxidate of oCFP. Fluorescence recovery studies may be performed as described (Reid et al., 1997). Denatured oCFPs may be prepared by incubating proteins in a denaturation buffer (8M urea and 1 mM DTT) at 95° C. for 5 min. For preparation of denatured/reduced oCFPs, 5 mM dithionite may be added to the denaturation buffer. Recovery of fluorescence may be initiated upon 100-fold dilution into a renaturation buffer (35 mM KCl, 2 mM $MgCl_2$, 50 mM Tris pH 7.5, 1 mM DTT) at 37° C. The emission at 475 nm can then be monitored by excitation at 435 nm for recovery, although various filters permit use of other wavelengths.

IV. Nucleic Acids and Expression Constructs

Certain embodiments of the present invention concern a nucleic acid encoding optimized cyan fluorescent proteins. In particular aspects, the nucleic acid is a cDNA. The term "nucleic acid" is well known in the art, and generally refers to a molecule (i.e., a strand) of DNA, RNA or a derivative or analog thereof. The term "nucleic acid" encompasses the terms "oligonucleotide" and "polynucleotide," each as a subgenus of the term "nucleic acid." The term "oligonucleotide" refers to a molecule of between about 3 to about 50 nucleobases in length. The term "polynucleotide" refers to at least one molecule of greater than about 50 nucleotides in length.

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 0 266 032, incorporated herein by reference, or via deoxynucleoside H-phosphonate intermediates as described by Froehler et al. (1986) and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al., 2001, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been partially or substantially isolated free of total genomic and in vitro reaction products. In certain embodiments, "isolated nucleic acid" also refers to a nucleic acid that has been isolated free the bulk of cellular components or in vitro reaction components. A nucleic acid may be purified on polyacrylamide gels, cesium chloride centrifugation gradients, or by any other means known to one of ordinary skill in the art (see for example, Sambrook et al., 2001, incorporated herein by reference).

In one embodiment, the present invention encompasses a nucleic acid that is complementary to a nucleic acid encoding a oCFP. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleotide sequence is capable of base-pairing with a single- or double-stranded nucleic acid molecule during hybridization. In certain embodiments, the term "complementary" refers to a nucleic acid that may hybridize to another nucleic acid strand or duplex in stringent conditions, as would be understood by one of ordinary skill in the art. In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

As used herein, "hybridization," "hybridizes" or "capable of hybridizing" is understood to mean the forming of a double or triple stranded molecule or a molecule with partial double or triple stranded nature. The term "anneal" as used herein is synonymous with "hybridize." The term "hybridization," "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

The present invention also concerns the isolation or creation of a recombinant construct or a recombinant host cell through the application of recombinant nucleic acid technology known to those of skill in the art or as described herein. A recombinant construct or host cell may comprise a nucleic acid encoding an oCFP. A "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is a nucleic acid engineered or altered by the hand of man, and generally comprises one or more nucleic acid sequences organized by the hand of man.

Functionally equivalent codons are codons that encode the same amino acid, such as the six codons for arginine and serine, and also refers to codons that encode biologically equivalent amino acids. For optimization of expression of in human cells, the codons are shown in Table 2 in preference of use from left to right. Thus, the most preferred codon for alanine is thus "GCC", and the least is "GCG." Codon usage for various organisms and organelles can be found at the website www.kazusa.orjp/codon/, incorporated herein by reference, allowing one of skill in the art to optimize codon usage for expression in various organisms using the disclosures herein. Thus, it is contemplated that codon usage may be optimized for other animals, as well as other organisms such as a yeasts, based on the preferred codon usage as known to those of ordinary skill.

TABLE 2

PREFERRED HUMAN DNA CODONS

| Amino Acids | | | Codons | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |

TABLE 2-continued

PREFERRED HUMAN DNA CODONS

| Amino Acids | | | Codons | | | | | |
|---|---|---|---|---|---|---|---|---|
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

It will also be understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

1. Vectors

As discussed above, the term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1990 and Ausubel et al., 1996, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression (see, for example Sambrook et al. 2001, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Table 3 lists non-limiting examples of elements/promoters that may be employed, in the context of the present invention, to regulate the expression of a RNA. Table 4 provides non-limiting examples of inducible elements, which are regions of a nucleic acid sequence that can be activated in response to a specific stimulus.

TABLE 3

| PROMOTER AND/OR ENHANCER | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |

TABLE 3-continued

PROMOTER AND/OR ENHANCER

| Promoter/Enhancer | References |
|---|---|
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $\alpha_1$-Antitrypsin | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 4

INDUCIBLE ELEMENTS

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor α | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Nonlimiting examples of such regions include the human LIMNK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki et al., 1998), DIA dopamine receptor gene (Lee et al., 1997), insulin-like growth factor II (Wu et al., 1997), and human platelet endothelial cell adhesion molecule-1 (Almendro et al., 1996).

Examples of promoters which are operative in bacterial cells include, a promoter of *Bacillus stearothermophilus* maltogenic amylase gene, *Bacillus licheniformis* α-amylase gene, *Bacillus amyloliquefaciens* BAN amylase gene, *Bacillus subtilis* alkaline protease gene, or *Bacillus pumilus* xylosldase gene; a $P_R$ or $P_L$ promoter of phage lambda; a lac, trp, or tac promoter of *Escherichia coli*; and the like.

Examples of promoters which are operative in insect cells include polyhedrin promoter, P10 promoter, basic protein promoter of *Autographa californica* nuclear polyhedrosis, baculovirus immediate early gene 1 promoter, baculovirus 39K delayed early gene promoter, and the like. Examples of promoters which are operative in yeast host cells include a promoter derived from yeast glycolysis system genes, alcohol dehydrogenase gene promoter, TPI1 promoter, ADH2-4c promoter, and the like.

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999; Levenson et al., 1998; and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable Markers

In certain embodiments of the invention, cells containing a nucleic acid construct of the present invention may be identified in vitro or in vivo by including a marker in the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. Further examples of selectable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392. Further useful plasmid vectors include pIN vectors (Inouye et al., 1985), and pGEX vectors, for use in generating glutathione S-transferase (GST) soluble fusion proteins for later purification and separation or cleavage. Other suitable fusion proteins are those with β-galactosidase, ubiquitin, and the like.

Another vector of interest is the "PEST" vector, pd4EGFP-Bid, from Clontech. This is a mammalian expression vector that encodes a fusion of destabilized enhanced green fluorescent protein (d4EGFP) and Bid, a member of the Bcl-2 "pro-apoptosis" family. Because of its fluorescent label, the Bid-d4EGFP fusion is easily detected by microscopy, allowing researchers to track its movements in response to certain apoptotic stimuli. To drive expression of the fluorescent fusion, pd4EGFP-Bid contains the immediate early promoter of cytomegalovirus, positioned just upstream of the Bid sequence. A short linker joins the Bid coding sequence to the 5'-end of d4EGFP. Farther downstream, the vector contains a pair of SV40 polyadenylation signals, which direct proper processing of the 3' end of the Bid-d4EGFP mRNA. The vector also contains an SV40 origin for replication in mammalian cells expressing the SV40 T antigen, a pUC origin of replication for propagation in E. coli, and an f1 origin for single-stranded DNA production. A neomycin-resistance cassette (Neo$^r$), consisting of the SV40 early promoter, the neomycin/kanamycin resistance gene of Tn5, and polyadenylation signals from the HSV TK gene, allows stably transfected eukaryotic cells to be selected using G418. A bacterial promoter upstream of the cassette confers kanamycin resistance (Kan$^r$) to E. coli. d4EGFP, a destabilized, red-shifted excitation variant of Aequorea victoria GFP, serves not only as a label, but also as a device to ensure protein turnover.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

2. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789, 215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322, 783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into Xenopus oocytes (Harland and Weintraub, 1985).

b. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

c. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

d. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

e. Sonication Loading

Additional embodiments of the present invention include the introduction of a nucleic acid by direct sonic loading. LTK⁻ fibroblasts have been transfected with the thymidine kinase gene by sonication loading (Fechheimer et al., 1987).

f. Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution.

Current formulations use a DNA condensing agent, such as protamine suflate, along with "helper lipids" (Reddy et al., 2002) describe a folate-targeted, cationic lipid based transfection complex was developed and found to specifically transfect folate receptor-expressing cells and tumors. These liposomal vectors were comprised of protamine-condensed plasmid DNA, a mixture of cationic and neutral lipids, and a folic acid-cysteine-polyethyleneglycol-phosphatidylethanolamine (FA-Cys-PEG-PE) conjugate. Overall, folate-labeled formulations produced an 8- to 10-fold increase in expression, as compared with the corresponding non-targeted cationic lipid/DNA formulations.

Hong et al. (1997) describe stable complexes of cationic liposomes with plasmid DNA were prepared by (1) including a small amount of polyethyleneglycol-phospholipid conjugate or (2) condensing the DNA with polyamines prior to the formation of liposome-plasmid complexes. These preparations were stable for months at 4° C. and gave reproducible high transfection activity for in vivo gene delivery. In these formulations cholesterol, not dioleoylphosphatidylethanolamine, was the helper lipid effective for sustaining high transfection activity in vivo.

Commercially available lipofection reagents include CellPhect Transfection Kit (Amersham-Pharmacia Biotech), CytoFectene Reagent (Bio-Rad), CLONrectin Reagent (Clontech), Cytofectin (Glen Research), Perfect Lipid™ Transfection Kit (Invitrogen), EuFectin (JBL Scientific), Lipofectamine™ 2000, Lipofectamine Plus™, Lipofectamine™, DMRIE-C Reagent (Life Technologies), ExGen 500 (MBI Fermentas), TransT LT-1 and LT-2 (PanVera), Transfast™ and Tr$_x$™ Reagents (Promega), SuperFect™ Transfection Reagent (Qiagen), LipoTAXI™ (Stratagene) and Genetransfer HMG-1,-2 Mixture (Wako Chemicals USA).

g. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

h. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

3. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art (see, for example, webpage phylogeny.arizona.edultree/phylogeny.html). A host cell into which the DNA or recombinant vector of the present invention is introduced may be a bacteria, yeast, fungi, or higher eukaryotic cell.

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expressioninclude, but are not limited to, bacteria, such as Gram-negatives like *E. coli* (e.g., *E. coli* strain RR1, *E. coli* LE392, *E. coli* B, *E. coli* X 1776 (ATCC No. 31537) as well as *E. coli* W3110 (F-, lambda-, prototrophic, ATCC No. 273325), DH5α, JM109, and KC8, Gram-positive bacteria such as *Streptomyces, Bacillus* species (e.g., *subtilis*); and other enterobacteriaceae such as *Salmonella typhimurium, Serratia marcescens*, various *Pseudomonas* specie, as well as a number of commercially available bacterial hosts such as SURE® Competent Cells and SOLOPACK™ Gold Cells (STRATAGENE®, La Jolla).

Other examples of fungal cells are filamentous bacteria, for example *Aspergillus, Neurospora*, and *Fusarium*, and cells belonging to Trichoderma. When a filamentous bacterium is used as a host cell, transformation can be performed by integrating the DNA construct into the host chromosome and obtaining a recombinant host cell. Integration of the DNA construct into the host chromosome can be performed according to a known method such as homologous recombination or heterologous recombination.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Examples of yeast cells include cells belonging to *Saccharomyces* or *Schizosaccharomyces*, and examples include *Saccharomyces cerevisae* and *Saccharomyces kluyveri*.

When an insect cell is used as a host, a protein can be expressed by co-transfecting a recombinant gene transduction vector and a baculovirus into the insect cell to obtain a recombinant virus in the insect cell culture supernatant, and then infecting the recombinant virus into the insect cell (for example, as described in Baculovirus Expression Vectors, 1988, and the like).

As a baculovirus, for example, *Autographa californica* nuclear polyhedrosis virus, which is a virus that infects Mamestra-family insects, and the like, can be used. As an insect cell, for example, Sf9 and Sf21, which are ovarian cells of *Spodoptera frugiperda*, and Hi Five, which is an ovarian cell of *Trichoplusia ni* (Invitrogen), or the like can be used.

4. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. No. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide.

It is contemplated that the proteins produced by the methods of the invention may be "overexpressed," i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide in comparison to the level in natural cells is indicative of overexpression, as is a relative abundance of the specific protein in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g., 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

V. Fluorescence Energy Transfer (FRET)

Two GFP variants, cyan fluorescent protein (CFP) and yellow fluorescent protein (YFP), have special fluorescence excitation and emission properties that are well suited to measurement of close molecular distances. When these two molecules are positioned at distances within 7 nm of each other, energy transfer can occur from the excited state of the donor molecule (CFP), to the unoccupied excited state of the acceptor molecule (YFP) by a process commonly referred to as fluorescence resonance energy transfer (FRET). FRET between CFP and YFP can be detected using a wide variety of spectroscopic and fluorescence microscopy techniques and is often used to report protein-protein interactions or changes in the conformation state of a peptide or protein. Since the efficiency of FRET is directly related to the spectroscopic properties of both the donor and acceptor molecules, improvements can be made to the fluorescence properties of the fluorophores, such as to increase both the FRET efficiency and the chances of successful detection. FRET has also been used to quantify association of a protein of interest with an organelle (Chiu et al., 2002).

The overall FRET efficiency is determined by several factors and is directly related to the amount of overlap between the absorption spectra of the acceptor molecule and the emission spectra of the donor molecule. The FRET efficiency is also affected by the ability of the donor molecule to absorb light, as indicated by its molar extinction coefficient, and the overall stability of the excited state, as indicated by the probability that absorption will lead to fluorescence (quantum yield) and the lifetime of the excited state. Although CFP is the most commonly used donor for FRET using fluorescent proteins, there are a number of disadvantages for its use in the FRET reaction. The molar extinction coefficient and the quantum yield of CFP are much less than the other commonly used fluorescent proteins. As a result CFP is typically 5-fold less bright than the acceptor molecule. Furthermore, CFP has two fluorescent states of unequal brightness. This results in a two-component excited-state fluorescence lifetime, which is disadvantageous for detection of FRET using fluorescence lifetime measurements. In addition, this leads to quenching of CFP fluorescence when it is in close proximity to another CFP molecule by a process known as homotransfer.

The present invention describes changes made to the spectroscopic properties of CFP that are specifically designed to improve the properties of CFP as a donor for FRET. Specifically, mutations were introduced into CFP in order to improve its molar extinction coefficient and quantum yield, and produce a single component excited state lifetime. The oCFP of the present invention is thus used as a donor fluorescent protein (DFP) for FRET studies. An acceptor fluorescent protein (AFP) may be green fluorescent protein, red fluorescent protein, yellow fluorescent protein, EGFP, EYFP, Venus, Citrine, phiYellow, copGreen CGFP, ECFP, oCFPs, fluoroscein, rhodamine, Oregon Green, or Alexa-488. In fact, practically any chromophore capable of resonance energy transfer with CFP, i.e., with absorbance between 450 and 600 nm, may be used, including dyes, fluorophores and non-fluorescent proteins that are capable of energy absorbance in the appopriate range (Forster, 1948; Patterson et al., 2000).

The types of the microscope can be suitably selected depending on the purpose. If frequent observations are necessary for monitoring a time course of the changing, conventional incident-light fluorescent microscope is preferred. If resolution is to be increased as in the case where detailed intercellular localization is to be monitored, confocal laser microscope is preferred. As a microscope system, an inverted microscope is preferred in view of keeping the physiological state of cell and preventing contamination. When erecting microscope is used, an immersion lens can be used in the case of using lens of high power.

The filter set can be suitably selected depending on the fluorescent wave length of the fluorescent protein. For the observation of GFP, it is preferred to use a filter with excitation light of about 470-490 nm and fluorescent light of about 500-520 nm. For the observation of YFP, it is preferred to use a filter with excitation light of about 480-500 nm and fluorescent light of about 510-550 nm. For the observation of CFP, it is preferred to use a filter with excitation light of about 425-445 nm and fluorescent light of about 460-500 nm.

Moreover, when time course observation is carried out in living cells by using a fluorescent microscope, the cells should be photographed in a short period, and therefore a high sensitive cooled CCD camera is used. By using a cooled CCD camera, thermal noise can be decreased by cooling CCD, and weak fluorescent image can be clearly photographed by exposure of short period.

VI. Screening Formats

The present invention facilitates various screening assays that utilize fluorescent proteins. Of particular interest are assays that track protein position within a cell, tissue, organ or organism. Such assays may comprise random screening of large libraries of candidate substances; alternatively, the assays may be used to focus on particular classes of compounds selected with an eye towards structural attributes that are believed to make them more likely to modulate the function of interest.

To identify a modulator, one generally will determine the function of interest in the presence and absence of the candidate substance, a modulator defined as any substance that alters function. For example, a method generally comprises:

(a) providing a candidate modulator;
(b) admixing the candidate modulator with a cell or a suitable experimental animal;
(c) measuring one or more characteristics of the compound, cell or animal in step (c); and
(d) comparing a characteristic measured in step (c) with the characteristic in the absence of said candidate modulator,
wherein a difference between the measured characteristics indicates that the candidate modulator is, indeed, a modulator of the characteristic.

As stated above, assays may be conducted in cell free systems, in isolated cells, tissues or organs, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

1. Modulators

As used herein the term "candidate substance" refers to any molecule that may potentially inhibit or enhance an activity or characteristic of interest. The candidate substance may be a protein or fragment thereof, a small molecule, or even a nucleic acid molecule. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators. Other suitable modulators include antisense molecules, ribozymes, and antibodies (including single chain antibodies), each of which would be specific for the target molecule.

2. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

Discussed elsewhere in this document are FRET assays, which provide excellent on the proximity of biomolecules.

3. In Cyto Assays

The present invention also contemplates the screening of compounds for their ability to modulate various functions in cells, including intracellular localization and trafficking. Depending on the assay, culture may be required. The cell is examined using any of a number of different physiologic assays. Alternatively, molecular analysis may be performed, for example, looking at protein expression, mRNA expression (including differential display of whole cell or polyA RNA) and others. Methods for examining the location of fluorescent proteins within cells are well known to those of skill in the art.

4. In Vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In one such assay, candidate substance labeled with a fluorescent protein is administered to an animal and its distribution is assesed. Alternatively, the distribution of labeled target molecule is assessed in the presence and absence of a candidate substance. Assessing may include obtaining a small sample (e.g., blood, urine, tissue) from an animal, or it may involve sacrificing the animal to obtain whole organ or even whole organism information.

VII. Kits

According to the present invention, there is provided a kit for analyzing localization of intercellular components and/or analyzing a physiologically active substance, which comprises at least one selected from the fluorescent protein, the fused fluorescent protein, DNA, the recombinant vector or the transformant as mentioned herein. The kit of the present invention can be prepared by known materials and techniques which are conventionally used in the art.

The reagent such as the fluorescent protein and DNA can be prepared in a form suitable for preservation by dissolving it in a suitable solvent. Examples of a suitable solvent include water, ethanol, various buffer solutions, and the like.

VIII. Examples

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials & Methods

Molecular Cloning. mCit was constructed from pEYFP-N3 and pEYFP-C1 (Clontech) using the Quikchange site-directed mutagenesis kit (stratagene). The A206K monomeric mutation (Zacharias et al., 2002) was made using sense primer 5'-GAGCACCCAGTCCAAACTGAGCAAA-GACC-3' (SEQ ID NO:1) and antisense primer 5'-GGTCTTTGCTCAGTTTGGACTGGGTGCTC-3' (SEQ ID NO:2). The Q69M Citrine mutation (Griesbeck et al., 2001) was made using sense primers 5'-CTTCGGCTACG-GCCTGATGTGCTTCGCCCGCTACC-3' (SEQ ID NO:3) and antisense primer as 5'-GGTAGCGGGCGAAGCACAT-CAGGCCGTAGCCGAAG-3' (SEQ ID NO:4). For bacterial expression, the His tagged expression vector, pQE-9 vector (Qiagen) was modified to create pQE9-N1 by removal of an existing NheI restriction site (sense primer 5'-GGTGAGAATCCAAGCTAGGTTGGC-GAGATTTTCAGG-3' (SEQ ID NO:5); antisense primer 5'-CCTGAAAATCTCGCCAACCTAGCTTG-GATTCTCACC-3' (SEQ ID NO:6)), and reintroduction of a NheI site into the multiple cloning site of the original vector (sense primer 5'-CCATCACCATCACGGGCTAGCCGAC-CTGCAGCC-3' (SEQ ID NO:7); antisense primer 5'-GGCTGCAGGTCGGCTAGCCCGTGATGGTGATGG-3' (SEQ ID NO:8)). A second modified vector (pQE9-N1-NotI) was additionally modified by introduction of a NotI site (sense primer 5'-GCTAGCCGACCTGCGGC-CGCGCTTAATTAGCTGAGC-3' (SEQ ID NO:9); antisense primer 5'-GCTCAGCTAATTAAGCGCGGCCG-CAGGTCGGCTAGC-3' (SEQ ID NO: 10)). ECFP then subcloned from pECFP-C1 into the pQE9-N1 vector using NheI and HindIII restriction sites to create a bacterial expression plasmid. Coupled dimers were generated by first subcloning ECFP from the pECFP-N3 plasmid into pQE9-N1-NotI using NheI and NotI restriction sites, followed by insertion of either mCit (from pmCit-C1) or ECFP (from pECFP-C1) using NheI and HindIII restriction sites. The resulting His-tagged constructs contain two fluorescent proteins separated by the linker SGLRSRAQASNSAVDG-TAGPGSPPVAT (SEQ ID NO:11). An identical strategy was used to create the ECFP(148D):ECFP(148D) construct. Mutations into ECFP in the pQE9-N1 vector were made using the following primers: S72A sense 5'-GCAGTGCT-TCGCCCGCTACCC-3' (SEQ ID NO:12), antisense 5'-GGGTAGCGGGCGAAGCACTGC-3' (SEQ ID NO:13); Y145D sense 5'-GGAGTACAACGACATCAGCCAC-3' (SEQ ID NO: 14), antisense 5'-GTGGCTGATGTCGTTG-TACTCC-3' (SEQ ID NO:15); H148D sense 5'-AACTA-CATCAGCGACAACGTCTATA-3' (SEQ ID NO:16), antisense 5'-TATAGACGTTGTCGCTGATGTAGTT-3'; (SEQ ID NO:17) Y145X sense 5'-GGAGTACAACNNCAT-CAGCGAC-3' (SEQ ID NO: 18), antisense 5'-GTCGCT-GATGNNGTTGTACTCC-3' (SEQ ID NO:19); Y145A sense 5'-GGAGTACAACGCCATCAGCGAC-3' (SEQ ID NO:20), antisense 5'-GTCGCTGATGGCGTTGTACTCC-3' (SEQ ID NO:21). ECFP variants were subcloned back into the mammalian expression vector pECFP-C1 using NheI and HindIII restriction sites, and into the pECFP-N3 vector using BamHI and BsrGI restriction sites after PCR using sense primer 5'-AAGGATCCCCACCGGTCGCC-3' (SEQ ID NO:22) and antisense primer 5'-TTGAGCTC-GAGATCGAGTCCGG-3' (SEQ ID NO:23). ECFP:mCit and Cerulean:mCit constructs were generated by subcloning ECFP and Citrine from the pQE9-N1 plasmids into pmCit- N3 using NheI and HindIII restriction sites. The linker separating the fluorescent proteins is identical to the one created for recombinantly generated protein. ECFP:GK: mCit and Cerulean:GK:mCit constructs were generated by first replacing EYFP of ECFP:GK:EYFP (Rizzo et al., 2002) with mCit from the pmCit-N3 plasmid using BamHI and NotI restriction sites. ECFP was then replaced by Cerulean from the pCerulean-C1 plasmid using NheI and BglII restriction sites. All enzymes were obtained from New England Biolabs and all ligations were performed using QuickLigase (NEB). DH5α bacteria were used to maintain mammalian expression constructs, and XL1-Blue bacteria were used to maintain plasmids containing bacterial expression promoters. DNA isolation was performed using QIAprep Spin Miniprep Kit (Qiagen) for plasmid purification and QIAquick Gel Extraction Kit for purification from agarose gels. Sequences were verified by restriction digest and sequencing reactions performed by the Vanderbilt-Ingram Cancer Center DNA Sequencing Shared Resource.

Protein Purification for Spectroscopic Analysis. His-tagged recombinant proteins were prepared using the M15 (pRep4) strain (Qiagen) of *E. coli*. Competent cells were generated and transformed according to the manufacturer's protocal. Pre-warmed volumes of 100 to 500 ml LB broth containing 25 mg/ml kanamycin (Sigma) and 50 mg/ml carbinicillin (Sigma) were inoculated with a 2.5% starter culture that was grown overnight from single colonies. Protein production was induced (OD=0.4) using 1 mM IPTG (RPI). Following 5 hours of culture at 37° C. in an orbital shaker (250 RPM), cultures were harvested, concentrated by centrifugation (20 min, 12,000 g, 4° C.), and frozen in a dry ice/ethanol bath. Frozen pellets were stored overnight at −80° C. Pellets were thawed on ice (15 min) prior to lysis using 5 ml Bugbuster Protein Extraction Reagent (Novagen) cocktail/gram of cell paste containing 25 units/ml Benzonase (Novagen), 1000 units/ml rLyzozyme (Novagen) and Protease Inhibitor Cocktail for use with Bacterial cells (Sigma) according to the manufacturer's recommendations. Cells were lysed by shaking for 20 min at room temperature, and insoluble material was removed by centrifugation (20 min/4000 g) in a microfuge. The cleared lysate was adjusted to 10 mM imidizole, and bound to 1 ml Ni—NTA agarose resin (Qiagen)/gram of cell paste by shaking at 300 RPM on an orbital shaker for 1 h (4° C.). The resin was then loaded on a disposable column, washed with 10 bed volumes of NPI-20 buffer (20 mM imidizole, 300 mM NaCl, 50 mM $NaH_2PO_4$ pH 8.0) by gravity flow. Proteins were eluted using NPI-250 buffer (250 mM imidizole, 300 mM NaCl, 50 mM $NaH_2PO_4$ pH 8.0) buffer. Protein concentration was quantified using the Advanced Protein Reagent (Cytoskeleton Inc.), and SDS-PAGE analysis.

Screening for Y145X mutations. Random mutations into position Y145 were incorporated into pQE9-N1/ECFP/S72A/148D and pQE9-N1/ECFP/S72G/148D by the method described above. Mutants were transformed into XL1-Blue competent cells, and cultured on Luria-Bertani (LB) media plates containing 140 mg/ml ampicillin. The overall brightness of individual colonies was assessed using a M²Bio fluorescent dissecting scope (Carl Zeizz Microimaging, Inc.) equipped with ECFP excitation and emission filters. 96 of the brightest colonies were collected and cultured overnight in a 96-well deep well dish. 20 μL of these starter cultures were used to inoculate 5 mls of LB media grown in 24 well plates. Cultures were induced ($OD_{600}$=0.6) using 0.5 mM IPTG overnight while shaking at 150 RPM at 37° C. Bacteria were harvested by centrifugation (30 min, 300 g, 4° C.), and frozen for 1 h at −20° C. Bacteria were then lysed, and the mutants were purified using Ni—NTA Superflow on the BioRobot 3000 (Qiagen) using the 1 mg native protein purification routine. 10 μL of purifed protein in 100 μl TE buffer (10 mM TrisCl, 1 mM EDTA, pH 8.0) were assayed for fluorescence (425 nm-455 nm excitation/top collection of 475-495 nm emission) using the Fusion Universal Microplate Analyzer (Packard) on a 96-well plate. Fluorescence was normalized to protein concentration and the 8 brightest colonies were selected for sequencing analysis and spectral analysis. Spectral analysis was performed on protein purified from larger volume cultures as described above.

Spectroscopy. Steady-state fluorescence measurements were acquired using a T-format spectrofluorometer (Photon Technologies Inc. QuantaMaster). Absorption measurements were acquired using the 8453 UV-Visible system (Hewlett-Packard). Fluorescence lifetimes and time-resolved anisotropy decays were acquired in TE buffer (pH 8.0) using a frequency doubled Ti:Sapphire laser (Coherent Mira) and a time-correlated single photon counting module (Edinburgh Instruments Lifespec-ps). Extinction coefficient was calculated using Beer's law and the absorbance at 433 nm in TE buffer (pH 8.0). Quantum yields was determined using emission at 450-575 nm (excitation at 440 nm) in comparison to an equal optical density of fluorescein (Molecular Probes; quantum yield=0.95) in TE buffer (pH 8.0) as a reference standard. Steady state anisotropy values were calculated (425 nm excitation, 477 nm collection) using the two-channel method.

pH Measurements. The $pK_a$ of Cerulean was determined through titration of 2 μg of protein in 100 μl pH titration buffer in 96 well plates using the Fusion Universal Microplate Analyzer as described above. The buffers for pH titration contained 125 mM KCl, 20 mM NaCl, 0.5 mM $CaCl_2$, 0.5 mM $MgCl_2$, and 25 mM of ethanolamine (pH 10.0, 9.5), TAPS (pH 9.0, 8.5), HEPES (pH 8.0, 7.5, 7.0), MES (pH 6.5, 6.0, 5.5), or acetate (pH 5.0, 4.5, 4.0). The pKa was calculated by curve-fitting of the data using Prizm software (Graphpad).

Cell Culture. COS-7 cells were cultured in DMEM (Gibco) supplemented with 10% FBS and antibiotics. The appropriate DNA (10 μg) was introduce by square-wave electroporation (10×50 μs, 300 V, 500-ms intervals) with a BTX ECM830 electroporator in a 4 mm gapped cuvette. Cells were then plated on 35 mM dishes containing No. 0 coverslips (Mat-Tek) for microscopic observation. Culture of βTC3 cells has been previously described (Rizzo et al., 2002).

Fluorescence Microscopy. Spectral imaging and histogram analysis was performed using an LSM510 META system (Carl Zeiss Microlmaging, Inc.) equipped with a S-M incubator (Carl Zeiss Microlmaging, Inc.) controlled by the CTI temperature regulator along with humidification. Temperature was maintained at 32° C. Imaging of COS7 cells was performed with 458 nm excitation provided by an Ar laser, and a 63×, 1.4 NA apochromat objective lens. Linear unmixing was performed using appropriate reference spectra for extraction of cyan and yellow channels in FIGS. 2A-E. For the FRETGK biosensors, 10 μg of plasmid DNA was electroporated into PTC3 cells 24 hours prior to analysis. Insulin treatment of starved cells was as previously described (Zhang et al., 2001). For these studies, multiphoton excitation (800 nm) was provided by a Mira 900 Ti:Saph laser (Coherent) in combination with spectral imaging as described above.

EXAMPLE 2

Results

Two fluorescent proteins derived from Aequorea, ECFP (Heim and Tsien, 1996) and YFP (Ormo et al., 1996), have appropriate fluorescence excitation and emission properties for the measurement of close molecular distances. When these two molecules are positioned approximately 5 nm (Patterson et al., 2000) apart, energy can transfer from the excited state of the donor fluorophore (ECFP), to the unoccupied excited state of the acceptor fluorophore (YFP). This strategy has been used to detect molecular interactions in living cells and is the basis for a wide variety of molecular biosensors (Zhang et al., 2002). In theory, this strategy is easily applied to a wide variety of biological problems. However, in practice, these assays are often quite problematic because of a small dynamic range. The change in the overall YFP to ECFP ratio is typically only 10-30% for most of the FRET-based indicators (Miyawaki et al., 1997; Ting et al., 2001; Zhang et al., 2001; Rizzo et al., 2002) with few notable exceptions (Vanderklish et al., 2000; Truong et al., 2001). This magnitude of contrast pushes the limit of modern digital microscopy, since the signal-to-noise level may often be in excess of 10% at low intensity levels (Swedlow et al., 2002).

The dim fluorescence of ECFP is one of the major disadvantages of using ECFP in FRET studies since it's use results in a low signal-to-noise ratio. Although current varieties of YFP, such as Citrine (Griesbeck et al., 2001) and Venus (Nagai et al., 2002), are quite bright, ECFP is 3-fold less bright than the most popular variant of green fluorescent protein, EGFP (Table 5), and is at about 5-fold less bright

TABLE 5

Fluorescent properties of ECFP variants

| Fluorescent Protein | $\lambda_{Abs}$ ($\epsilon$) | $\lambda_{Em}$ (QY) | $pK_a$ | Relative Brightness |
|---|---|---|---|---|
| ECFP | 433 (29000) | 474 (37) | 4.7 | 1 |
| ECFP/H148D | 433 (32000) | 474 (68) | ND | 2 |
| D10 (ECFP/S72A/Y145G/H148D) | 433 (44000) | 474 (46) | ND | 1.9 |
| Cerulean (ECFP/S72A/Y145A/H148D) | 433 (43000) | 474 (62) | 4.7 | 2.5 |
| EGFP | 489 (55000) | 508 (60) | 5.9 | 3.1 |

One solution to the poor signal-to-noise ratio of intensity-based FRET measurement approaches is the adaptation of intensity-independent approaches to the measurement of FRET in biological specimens, such as fluorescence lifetime microscopy (Sekar and Periasamy, 2003). Since the presence of a FRET acceptor molecule (i.e., YFP), reduces the overall lifetime of the FRET donor (i.e., ECFP), the FRET reaction can be successfully detected by measuring change in the fluorescence lifetime of the donor molecule. To examine the suitability of using ECFP as a probe for lifetime-FRET measurements, the inventors used time-correlated single photon counting spectroscopy to measure the fluorescence lifetime decays of ECFP and a mCit:ECFP fusion protein (Table 6). Unfortunately, the fluorescence lifetime decay of ECFP does not fit to a single-component fluorescence lifetime decay, suggesting that ECFP has more than one fluorescent state. The inventors also found a fusion between two ECFP molecules also reduced the fluorescence lifetime. This suggests that the energy transfer between a ECFP:ECFP pairing is not homotransfer between identical fluorescent states.

TABLE 6

Summary of Fluorescence Lifetime Data

| | Single component fit | | | Two component fit | | | | | |
|---|---|---|---|---|---|---|---|---|---|
| Construct | $\tau_1$ (ns) | SD (ns) | $\chi^2$ | $\tau_1$ (ns) | SD (ns) | rel. % | $\tau_2$ (ns) | SD (ns) | rel. % | $\chi^2$ |
| ECFP | 3.0 | 0.0050 | 4.0 | 3.6 | 0.0327 | 86 | 1.2 | 0.0432 | 14 | 1.2* |
| ECFP (148D) | 3.6 | 0.0062 | 2.0* | | | | | | | |
| Cerulean | 3.3 | 0.0053 | 2.3* | | | | | | | |
| ECFP:ECFP | 2.8 | 0.0045 | 4.4 | 3.5 | 0.0399 | 80 | 1.4 | 0.0415 | 20 | 1.2* |
| ECFP(148D):ECFP(148D) | 3.5 | 0.0058 | 1.9* | | | | | | | |
| Cerulean:Cerulean | 3.3 | 0.0053 | 2.0* | | | | | | | |
| mCit:ECFP | 2.3 | 0.0050 | 9.1 | 3.2 | 0.0385 | 71 | 1.1 | 0.0263 | 29 | 1.3* |
| mCit:Cerulean | 2.5 | 0.0052 | 6.4 | 3.4 | 0.0627 | 68 | 1.4 | 0.0409 | 32 | 1.4* |

*increased components did not significantly improve fit than even the early generations of YFP (Patterson et al., 2001). FIG. 1A shows the emission spectra taken from a cell expressing a FRET pairing consisting of ECFP fused to a monomeric variant (Zacharias et al., 2002) of the Citrine YFP (mCit). Even though excitation parameters favor ECFP excitation, the peak intensity of mCit is over twice that of ECFP.

To detect the presence of energy transfer in ECFP:ECFP, we compared the time-resolved fluorescence anisotropy decay of the ECFP:ECFP with monomeric ECFP (FIG. 1B). The anisotropy decay was faster for the ECFP:ECFP and the inventors also detected a reduced steady-state anisotropy for the ECFP:ECFP (r=0.268) compared to ECFP alone (r=0.292). The inventors also found a ~10% reduction in the total fluorescence of the ECFP:ECFP compared to ECFP alone (FIG. 1C). This proportion is in agreement with the amount of energy transfer detected by our fluorescence lifetime measurements (FRET efficiency=9.3%). These results indicate the presence of energy transfer within the ECFP:ECFP and is consistent with two separate fluorescence state present. The existence of multiple states in different ECFP molecules will greatly complicates the use of fluorescence lifetime as an assay for FRET, even for ECFP:YFP.

The presence of two fluorescent states in ECFP is likely due to the two different conformations found in the crystal structure of ECFP (Hyun Bae et al., 2003). The two conformations result from alternate displacement of two hydrophobic residues (Y145 and H148) to the solvent exposed surface of the protein. Thus, the inventors hypothesized that mutation of one these residues to an amino acid with a hydrophilic side chain would stabilize a single conformation, and thus produce a cyan fluorescent protein with a single component fluorescence lifetime decay. Mutation of H148 to asparate was successful in producing a single component fluorescence lifetime decay (Table 6). In addition, the fluorescence lifetime of ECFP(H148D):ECFP (H148D) was comparable to that of the monomer. Therefore, the ECFP(H148D) variant is a much more suitable FRET donor for fluorescence lifetime studies.

The inventors next looked to increase the overall brightness and usefulness of ECFP(H148D). The invenetors then incorporated a mutation known to improve the folding of fluorescent proteins at 37° C. (S72A) (Cubitt et al., 1999), and performed random mutagenesis studies on Y145. The brightest variant isolated (clone D10) was found to have an improved molar extinction coefficient, although a reduced quantum yield (Table 5). Since DNA sequencing revealed substitution of Y145 with glycine in the D10 variant, we reasoned that a Y145A mutation would provide additional stability. The resulting variant (ECFP/S72A/Y145A/H148D), which was Cerulean, is 2.5-fold brighter than ECFP (Table 5) and has a single component fluorescence lifetime decay (Table 6), making it more suitable as FRET donor than ECFP, particularly for lifetime applications. In addition, the excitation and emission spectra of Cerulean are not different that ECFP, and no energy loss was observed in the homodimer (Table 6).

To compare the suitability of Cerulean and ECFP as FRET donors using a conventional, intensity-based imaging approach, constructs containing mCit fused to Cerulean and ECFP were expressed in COS-7 cells, and the relative intensities of donor (cyan) and acceptor (yellow) fluorescence was monitored under cyan excitation (FIGS. 2A-B). Cerulean was found be greater than 2-fold brighter than ECFP in living cells, and was of comparable intensity to mCit fluorescence. Thus, the inventors hypothesized that FRET studies incorporating Cerulean will have a greater signal-to-noise ratio compared to studies incorporating ECFP. To test this, they incorporated Cerulean into a FRET-based biosensor that reports changes in glucokinase (GK) conformations (Rizzo et al., 2002). When expressed in the βTC3 immortalized pancreatic β cell line, activation of GK by insulin results in decreased FRET between cyan and yellow fluorescent proteins placed on opposing ends of GK (FIG. 2C). Spectral information was collected from cells using spectral imaging before and after insulin stimulation. Although the mean spectral changes of the ECFP GK sensor (FIG. 2D) are similar in magnitude to spectral changes that occur in the Cerulean GK sensor, much less variance is found in the data collected using the Cerulean GK sensor. The difference between pre- and post-insulin stimulation using the Cerulean GK sensor was found to be statistically significant (p<0.05, t-test), whereas the results obtained using the ECFP GK sensor were not found to be significant by the same test. Since the increased brightness of Cerulean results in an improved signal-to-noise ratio, it is a superior to ECFP as a FRET donor.

EXAMPLE 3

Materials and Methods

Recombinant DNA procedures. The monomeric mutation A206K (Zacharias et al., 2002) was introduced into fluorescent proteins using the Quikchange kit (Stratagene) using the following primer sets: mEGFP (sense 5' CTGAGCACCCAGTCCAAACTGAGCAAAGACCCC 3' (SEQ ID NO:24), antisense 5' GGGGTCTTTGCTCAGTTTGGACTGGGTGCTCAG 3' (SEQ ID NO:25)), mVenus (5' CTGAGCTACCAGTCCAAACTGAGCAAAGACCCC 3' (SEQ ID NO:26), antisense primer 5' GGGGTCTTTGCTCAGTTTGGACTGGTAGCTCAG 3' (SEQ ID NO:27)), mCerulean sense 5' GCACCCAGTCCAAGCTGAGCAAAGA 3' (SEQ ID NO:28), antisense primer 5' TCTTTGCTCAGCTTGGACTGGGTGC 3' (SEQ ID NO:29)), mCitrene (sense primer 5' CTGAGCTACCAGTCCAAACTGAGCAAAGACCCC 3' (SEQ ID NO:30) and antisense primer 5' GGGGTCTTTGCTCAGTTTGGACTGGTAGCTCAG 3' (SEQ ID NO:31)). Fluorescent proteins not already in the C1 vector were amplified by PCR and subdloned into the C1 vector by excision of EGFP from the pEGFP-C1 vector. mVenus-C1 was generated using AgeI and BsrGI restriction digest of the PCR product obtained from sense primer (5' TTTACCGGTCGCCACCATGGTGAG 3' (SEQ ID NO:32)) and antisense primer (as 5' TTCTTACTTGTACAGCTCGTCCATGCCG 3' (SEQ ID NO:33)). CopGFP was amplified from the pCop-Green-C plasmid (Evrogen) (sense primer 5' TTTAGTGAACCGTCAGATCCGC 3' (SEQ ID NO:34), anti-sense primer 5' AATCCGGAGGCGAAGGCG 3' (SEQ ID NO:35)) and subdloned into the C1 vector using NheI and BspEI restriction sites. Generation of phiYFP-C1 and phiYFPm-C1 were preceded by the introduction of silent mutations to remove key restriction sites in the cDNA. Two BsrGI sites (1029G->C: sense primer-5' TGGCAGCGTCTACAATCGCG 3' (SEQ ID NO:36), antisense primer 5' ACGCGATTGTAGACGCTGCC 3' (SEQ ID NO:37) 1122G->C sense primer-5' CCCACTGCCTCTACATCTGG 3' (SEQ ID NO:38), antisense primer 5' CCAGATGTAGAGGCAGTGGG 3' (SEQ ID NPL39)) and a BglII site (1173C->T sense primer 5'CCTTCAAGATTTGCCACGAG 3' (SEQ ID NO:40), antisense primer 5'CTCGTGGCAAATCTTGAAGG 3' (SEQ ID NO:41)) were first removed using the Quikchange site-directed mutagenesis kit. To generate phiYFP-m, the same approach was used to introduce 3 additional mutations into phiYFP (K221T: sense primer-5' TATGAGCCTGACGGAGACCGTGC 3' (SEQ ID NO:42), antisense primer-5' GCACGGTCTCCGTCAGGCTCATA 3' (SEQ ID NO:43); T170A: sense primer 5' CCACGAGATCGCCGGCAGCAA 3' (SEQ ID NO:44), antisense primer 5' TTGCTGCCGGCGATCTCGTGG 3' (SEQ ID NO:45); N21D: sense-5' GATGGAGGGCGATGTGGATGG 3' (SEQ ID NO:46), antisense primer 5' CCATCCACATCGCCCTCCATC 3' (SEQ ID NO:47)). The modified phiYFP and phiYFPm were then subcloned into the C1 vector (sense primer: 5' AAAGCTAGCGCTACCGGTCGCCACC 3' (SEQ ID NO:48), antisense primer 5' TTTTCCGGACAGGTAG-GTCTTGC 3' (SEQ ID NO:49); NheI/BspEI fragment).

A series of N3 vectors were generated from the pEGFP-N3 by replacing EGFP with PCR products amplified from C1 vectors using BamHI and BsrGI restriction sites. For Aequorea GFP derived vectors, sense primer 5' AAGGATC-CCCACCGGTCGCC 3' (SEQ ID NO:50) and antisense primer 5' TTGAGCTCGAGATCTGAGTCCGG 3' (SEQ ID NO:51) were used. PhiYFP and phiYFPm were amplified using sense primer-5' AAGGATCCCCACCGGTCGCC 3' (SEQ ID NO:52) and antisense primer 5' AAGAACATG-TACAGGTAGGTCTTGC 3' (SEQ ID NO:53). CopGFP was amplified using sense primer 5' AAGGATCCCCAC-CGGTCGCC 3' (SEQ ID NO:54) and antisense 5' TTCT-TGTACATGGCGAAGGCGATG 3' (SEQ ID NO:55).

His-tagged monomeric fluorescent proteins were generated by insertion of the coding sequences from the C1 vectors into the pQE-N1 vectors using NheI and HindII restriction sites. His-tagged coupled FRET pairings were generated by first cloning donor fluorophores (mCerulean, mEGFP, and copG) were then subcloned from the N3 vector into the bacterial expression plasmid pQE-NI-NotI (Rizzo et al., 2004) using NheI-NotI restriction sites. Acceptor fluorophores were added either by ligating the NheI-BglII fragment from C1 vectors to a NheI-BamHI digested plasmid to generate a short linker with the sequence SGLRSP-PVAT (SEQ ID NO:56), or by ligating a NheI-BamHI fragment from a C1 vector to NheI-BglII digested plasmid to generate a long linker with the sequence SGL-RSRAQASNSAVDGTAGPGSRAQASN-SAVDGTAGPGSPPVAT (SEQ ID NO:57). Mammalian expression coupled FRET pairs were generated by ligating the NheI-BglII fragment from C1 vectors to a NheI-BamHI digested N3 donor plasmid to generate a short linker, or by ligating a NheI-BamHI fragment from a C1 vector to NheI-BglII digested N3 donor plasmid to generate the long linker.

All enzymes were obtained from New England Biolabs and all ligations were performed using QuickLigase (NEB). DH5α bacteria were used to maintain mammalian expression constructs, and XL1-Blue bacteria were used to maintain plasmids containing bacterial expression promoters. DNA isolation was performed using QIAprep Spin Miniprep Kit (Qiagen) for plasmid purification and QIAquick Gel Extraction Kit (Qiagen) for purification from agarose gels. Sequences were verified by restriction digest and sequencing reactions performed by the Vanderbilt-Ingram Cancer Center DNA Sequencing Shared Resource.

Protein Purification and Spectroscopy. His-tagged recombinant proteins were prepared using M15(pRep4) cells (Qiagen) and purified using Ni—NTA agarose resin as previously described (Rizzo et al., 2004). Protein concentration was quantified using the Advanced Protein Reagent (Cytoskeleton Inc.), and SDS-PAGE analysis and standardized using protein solutions of BSA and fluorescent proteins of known concentration. Sample purity was assessed by SDS-PAGE analysis and determined to be greater than 95%.

Steady-state fluorescence measurements were acquired using a T-format spectrofluorometer (Photon Technologies Inc.). Absorbance measurements were acquired using the 8453 UV-Visible system (Hewlett-Packard). Extinction coefficients were calculated from applying Beer's law to the peak absorbance (in TE buffer (pH 8.0)) of three separate concentrations of protein taken in quadruplicate. Linear regression analysis was used to generate extinction coefficients from the slope of protein concentration vs. absorbance plots. Molar concentrations were calculated from the theoretical protein sequence using the Peptide Properties calculator (www.basic.nwu.edulbiotools/ProteinCalc.html). Quantum yields were determined from integrated fluorescence spectra taken from an equal absorbance of a fluorescein reference standard (Molecular Probes; quantum yield=0.95) in TE buffer (pH 8.0). Measurements were performed in quadruplicate on solutions with equivalent absorbance (<0.05) and corrected for background fluorescence and differences in excitation intensity. Fluorescence lifetimes were acquired in TE buffer (pH 8.0) using a frequency doubled Ti:Sapphire laser (Coherent Mira) and a time-correlated single photon counting module (Edinburgh Instruments Lifespec-ps). Fluorescence lifetime measurements were collected at 475 nm (2 mm slits (~8 nm bandwidth) using 425 nm excitation for EYFP:ECFP coupled dimers, mCerulean, mVenus:mCerulean coupled dimers, mCitrene:mCerulean coupled dimers, and phiYF-Pm:mCerulean coupled dimers. A collection wavelength of 470 nm was used for mEGFP: mCerulean coupled dimers (425 nm excitation), and 465 nm light was collected for copGFP:mCerulean coupled dimers. A wavelength of 445 nm was used for excitation of EGFP, mEGFP, copGFP, mVenus:mEGFP coupled dimers, mVenus:copGFP coupled dimers, mCitrene:mEGFP coupled dimers and mCitrene: copGFP coupled dimers (495 nm emission). For mCitrene and mVenus, 445 excitation was used with 530 nm collection. 535 nm collection was used for phiYFP and phiYFPm detection (445 nm excitation). Magic angle conditions (0° polarized excitation, 54.7° polarized collection) were used in order to eliminate the effect of polarization. Curve fitting was performed using the F900 software (Edinburgh Instruments). Reported values are the average of 4 measurements.

FRET efficiency (E) was calculated from the fluorescence lifetime measurements using the equation:

$$E = 1 - \frac{\tau_{DA}}{\tau_D} \quad (1)$$

where $\tau_D$ is the fluorescence lifetime of the donor and $\tau_{DA}$ is the fluorescence lifetime of the donor in the presence of the acceptor (Clegg, 1992).

Calculation of Förster distances. Forster distances, $r_0$, were calculated from the Forster equation by the method of Patterson et al. (2000).

$$r_0^6 = \frac{9}{4(2\pi)^5} \frac{2303}{N} \kappa^2 \phi_D n^{-4} \int_0^\infty F_D(\lambda)\varepsilon_A(\lambda)\lambda^4 d\lambda \quad (2)$$

where 2303 is ln 10×1000 cm³, N is Avogadro's Number, $\kappa^2$ is orientation factor, $\phi_D$ is the quantum yield of the donor, n is the refractive index. The constants preceding $\kappa^2$ have a value of 8.786×10⁻¹¹ mol L⁻¹ cm nm². Within the spectral overlap integral, $F_D(\lambda)$ is the fluorescence emission intensity normalized such that its integral over wavelength is unity, and $\varepsilon_A$ is the extinction coefficient of the acceptor. Förster distances were calculated assuming randomization of dipole orientations ($\kappa^2$ equal to ⅔), and the index of refraction was set at the value used for water at 25° C. (n=1.3342).

The overlap integral was calculated from normalized donor emission and acceptor excitation spectra. Donor emission spectra were obtained using the following conditions: 425 nm excitation, 440 nm-600 nm emission for mCerulean and ECFP; 440 nm excitation, 455 nm-600 nm emission for copGFP; 450 nm excitation, 465 nm-600 nm emission for mEGFP; 450 nm excitation, 465 nm-620 nm emission for mCitrene, mVenus, and EYFP; 455 nm excitation, 470 nm-620 nm emission for phiYFPm. Acceptor excitation spectra were obtained using the following conditions: 350 nm-485 nm excitation, 500 nm emission for mCerulean and ECFP; 350 nm-525 nm excitation, 545 nm emission for mEGFP and copGFP; 350 nm-545 nm excitation, 565 nm emission for EYFP, mCitrene, and mVenus; 350 nm-560 nm excitation, 575 nm emission for phiYFPm.

EXAMPLE 4

Results

Properties of coupled FRET pairs. Fluorescence properties were determined for several fluorescent proteins that constitute the current set of useful FRET donors and acceptors for energy transfer measurements employing two different autofluorescent proteins (Table 7). Our set includes most commonly used set of the first generation cyan (ECFP) (Heim and Tsien, 1996) and yellow (EYFP) fluorescent proteins (Ormo et al., 1996), in addition to the monomeric variants of the newer generation of cyan (Cerulean (Rizzo et al., 2004)), and yellow fluorescent proteins (Citrene (Griesbeck et al., 2001) and Venus (Nagai et al., 2002)). The inventors also included the monomeric variant of the most widely used green fluorescent protein (EGFP) in addition to two species of fluorescent proteins derived from coral (copGFP and phiYFP) (Shagin et al., 2004) that have been recently become commercially available and are currently marketed as true monomers. Introduction of the monomeric A206K mutation (Zacharias et al., 2002) in Aequorea-derived fluorescent proteins (Cerulean, EGFP, Citrene, Venus) did not have an effect on the extinction coefficient and quantum yield to EGFP and Cerulean. The newer monomeric yellow variants were found to have an increased extinction coefficient but reduced quantum yield compared to previous generations. These effects were similar in magnitude to the effect on the EYFP(Q69K) variant that was reported by Zacharias et al. (2002), and did not affect the overall brightness.

To compare the efficiency of transfer between various acceptor-donor pairs, we generated fusion proteins consisting of a single acceptor fused to a single donor and separated by either a short 10 amino acid linker or a long 44 amino acid linker. These coupled FRET pairs were then bacterially expressed and purified. As shown by the fluorescence emission spectra (FIG. 1) and decreased donor fluorescence lifetime (Table 8), energy transfer was greater for the short-linker fusion proteins. Coupled FRET pairs containing two Aequorea-derived fluorescent proteins tolerated fusion and produced effects energy transfer consistent with vary appropriately with the linker size. Purification of the coral reef derived proteins, copGFP and phiYFP, was hindered by extensive aggregation of the individual proteins and fusions containing either variant. In addition, fusion of either protein to a second energy transfer pair produced unexpected effects on their fluorescence properties. In the donor position, copGFP developed a second fluorescence lifetime component. Fusion of PhiYFP with a second energy transfer pair disrupted maturation of fluorescence in either the donor or acceptor position (data not shown). Site-directed mutagenesis was also used to modify phiYFP to facilitate the generation of N-terminal fusions. This second generation phiYFP (phiYFPm) was found to less bright than phiYFP, and did not tolerate fusion to a donor fluorescent protein, as evidence by the absence of energy transfer from mCerulean (FIG. 3G, Table 8).

Förster distances calculation. Using fluorescence lifetime measurements of the donor fluorescent protein, we calculated FRET efficiencies for each of the coupled FRET pairings. Among the Aequorea-derived fluorescent proteins, the most efficient energy transfer was observed between mCerulean and mVenus (Table 8), The magnitude of the decrease in FRET observed by increasing the linker size was similar for all FRET pairings. Förster distances were calculated for the various donor-acceptor pairs to help assess whether the experimentally observed FRET efficiencies reflected the theoretical effects on the Förster distances resulted from swapping donor and acceptors (Table 9). A large increase in the Förster distance was observed by exchanging proteins with a low quantum yield donor (ECFP) for a high quantum yield fluorescent protein (mCerulean). In contrast, a much smaller increase is seen by exchanging EYFP for a more recent generation mCitrene or mVenus (FIG. 4).

Discussion. FRET experiments that exclusively use fluorescent proteins are required to be both bright, to give a high signal-to-noise ratio, and essentially monomeric, to ensure that the properties of the fluorescent proteins do not interfere with the measurement of energy transfer. These guidelines led to the exclusion of several commonly used fluorecent proteins from our analysis, namely the very dim blue and monomeric red fluorescent proteins (Campbell et al., 2002), and the obligate oligomers dsRed and HcRed. We also find that the current generation of copGFP and phiYFP proteins should also be excluded at this point in time, since the tendency of these proteins towards aggregation make generation of fusion proteins very difficult. Although the fluorescence properties of these proteins make them highly desirable for FRET assays, we have observed a variety of unexpected results that make even the simplest FRET experiments are very difficult to interpret. Using copGFP as a C-terminal fusion produces a two-compononet fluorescence lifetime that is very different than the single component lifetime of the untagged-protein. PhiYFP proteins were even harder to use as an epitope tag, and were unable to obtain reliable fluorescence with either the first generation phiYFP or the improved phiYFPm despite several attempts.

The Aequorea-derived varieties of fluorescent proteins are currently the best-characterized and most reliable variants for use in FRET experiments. As a FRET donor, we observed the best results using the monomeric variant of Cerulean. Since its quantum yield is 50% greater than ECFP, there is a large increase in the Förster distance when mCerulean is exchanged for ECFP as a FRET donor. Surprisingly, we did not observe greater efficiency using from MEGFP in our lifetime measurements. This may be due in part to inherent structural differences between EGFP and Cerulean that influence the relative orientation to the FRET acceptor. Even though energy transfer is more efficient using mEGFP over mCerulean along with a yellow fluorescent protein acceptor, the extensive spectral overlap makes changes to the overall spectra less evident than for the mCerulean donor (compare FIG. 3C with FIGS. 3D and 3E. In addition, the optimized wavelength for a mEGFP:yellow acceptor pairing is 20 nm below the peak excitation of mEGFP, as opposed to less than 10 nm for the optimized excitation wavelength of an equivalent mCerulean pairing.

TABLE 7

Properties of Fluorescent Proteins

| Fluorescent Protein | ε(φ) | Single component fit | | | Two component fit | | | | |
|---|---|---|---|---|---|---|---|---|---|
| | | $\tau_1$ (SD) | $\chi^2$ | $\tau_1$ (SD) | rel. % | $\tau_2$ (SD) | rel. % | $\chi^2$ | |
| ECFP | 29000 (0.37) | 3 (0.005) | 4 | 3.6 (0.033) | 86 | 1.2 (0.043) | 14 | 1.2* | |
| Cerulean | 43000 (0.62) | 3.42 (0.0083) | 1.44* | | | | | | |
| mCerulean | 44000 (0.62) | 3.40 (0.0110) | 1.44* | | | | | | |
| EGFP | 55000 (0.60) | 2.93 (0.0066) | 1.19* | | | | | | |
| mEGFP | 55000 (0.62) | 2.93 (0.0066) | 1.21* | | | | | | |
| copGFP | 70000 (0.60) | 2.74 (0.0061) | 1.24* | | | | | | |
| EYFP | 84000 (0.61) | | | | | | | | |
| Citrene | 77000 (0.76) | | | | | | | | |
| mCitrene | 90000 (0.62) | 3.67 (0.0089) | 1.30* | | | | | | |
| Venus | 92000 (0.57) | | | | | | | | |
| mVenus | 96000 (0.52) | 3.37 (0.0078) | 1.29* | | | | | | |
| phiYFP | 115000 (0.60) | 2.82 (0.0037) | 3.34 | 3.15 (0.029) | 90.5 | 1.22 (0.063) | 9.5 | 1.61* | |
| phiYFPm | 107000 (0.22) | 3.69 (0.0101) | 1.29* | | | | | | |

Fluorescence lifetime values were determined from recombinant protein purified to greater than 95% homogeneity using time-correlated single photon counting spectroscopy. Extinction coefficients (E) is expressed in $M^{-1}\,cm^{-1}$ and φ indicates the quantum yield. Relative % is the normalized relative contribution of the fluorescent species characterized by its fluorescence lifetime constant τ. Error is reported as standard deviation of the fit (SD) and goodness of fit is reported by $\chi^2$. *Increased components did not significantly improve fit according to the conventional τ/2 criteria.

TABLE 8

Properties of Coupled Fluorescent Proteins

| Acceptor:Donor linker | Single component fit | | Two component fit | | | | | E |
|---|---|---|---|---|---|---|---|---|
| | τ (SD) | $\chi^2$ | $\tau_1$ (SD) | rel. % | $\tau_2$ (SD) | rel. % | $\chi^2$ | |
| EYFP:ECFP | | | | | | | | |
| Short | 2.64 (0.0038) | 4.04 | 3.24 (0.0234) | 82.7 | 1.10 (0.0255) | 17.3 | 1.16* | 0.120 |
| Long | 2.81 (0.0035) | 4.37 | 3.33 (0.0185) | 86.6 | 1.06 (0.0243) | 13.4 | 1.16* | 0.063 |
| mVenus:mCerulean | | | | | | | | |
| Short | 2.77 (0.0115) | 1.24* | | | | | | 0.185 |
| Long | 2.99 (0.0112) | 1.26* | | | | | | 0.121 |
| mCitrene:mCerulean | | | | | | | | |
| Short | 2.89 (0.0114) | 1.26* | | | | | | 0.150 |
| Long | 3.01 (0.0106) | 1.33* | | | | | | 0.115 |
| phiYFPm:mCerulean | | | | | | | | |
| Short | 3.35 (0.0117) | 1.33* | | | | | | 0.015 |
| Long | 3.37 (0.0114) | 1.27* | | | | | | 0.009 |
| mEGFP:mCerulean | | | | | | | | |
| Short | 2.98 (0.0108) | 1.31* | | | | | | 0.124 |
| Long | 3.11 (0.0107) | 1.25* | | | | | | 0.085 |
| copGFP:mCerulean | | | | | | | | |
| Short | 2.59 (0.0093) | 1.33* | | | | | | 0.238 |
| Long | 2.94 (0.0097) | 1.26* | | | | | | 0.135 |
| mVenus:mEGFP | | | | | | | | |
| Short | 2.44 (0.0077) | 1.30* | | | | | | 0.167 |
| Long | 2.56 (0.0068) | 1.25* | | | | | | 0.126 |
| mCitrene:mEGFP | | | | | | | | |
| Short | 2.50 (0.0077) | 1.34* | | | | | | 0.147 |
| Long | 2.60 (0.0069) | 1.33* | | | | | | 0.113 |
| mVenus:copGFP | | | | | | | | |
| Short | 1.53 (0.0066) | 4.63 | 2.47 (0.0395) | 60.1 | 0.69 (0.0159) | 39.9 | 1.11* | 0.442 |
| Long | 1.60 (0.0042) | 3.94 | 2.10 (0.0245) | 67.7 | 0.81 (0.0215) | 32.3 | 1.09* | 0.416 |

TABLE 8-continued

Properties of Coupled Fluorescent Proteins

| Acceptor:Donor linker | Single component fit | | Two component fit | | | | | E |
|---|---|---|---|---|---|---|---|---|
| | $\tau$ (SD) | $\chi^2$ | $\tau_1$ (SD) | rel. % | $\tau_2$ (SD) | rel. % | $\chi^2$ | |
| mCitrene:copGFP | | | | | | | | |
| Short | 2.33 (0.0070) | 3.74 | 2.84 (0.0250) | 84.6 | 0.72 (0.0253) | 15.4 | 1.10* | 0.150 |
| Long | 1.74 (0.0041) | 4.32 | 2.32 (0.0298) | 66.9 | 0.92 (0.0233) | 33.1 | 1.20* | 0.365 |

Fluorescence lifetime values were determined from recombinant protein purified to greater than 95% homogeneity using time-correlated single photon counting spectroscopy. Relative % is the normalized relative contribution of the fluorescent species characterized by its fluorescence lifetime constant $\tau$. Error is reported as standard deviation of the fit (SD) and goodness of fit is reported by $\chi^2$. *Increased components did not significantly improve fit according to the conventional $\tau/2$ criteria. (E) was calculated as from the single component fits as described in the Methods.

TABLE 9

Calculated Förster Distances (nm)

| Donor | Acceptor | | | | | | |
|---|---|---|---|---|---|---|---|
| | EYFP | mVenus | mCitrene | phiYFPm | mEGFP | copGFP | mCerulean |
| ECFP | 4.89 | 4.95 | | | | | |
| mCerulean | 5.33 | 5.40 | 5.36 | 5.49 | 5.03 | 4.99 | 3.52 |
| mEGFP | | 5.71 | 5.65 | 5.84 | 4.53 | 3.96 | 1.69 |
| copGFP | | 5.61 | 5.57 | 5.72 | 4.80 | 4.34 | 1.95 |
| phiYFPm | | 3.91 | 3.83 | 4.46 | 2.27 | 1.87 | 0.83 |
| mCitrene | | 5.15 | 5.05 | 5.67 | 3.09 | 2.51 | 1.33 |
| mVenus | | 4.95 | 4.85 | 5.48 | 2.84 | 2.20 | 1.09 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

IX. References

The following references, to the extent that they provide exemplary procedural or other details supplementary to those set forth herein, are specifically incorporated herein by reference:

U.S. Pat. No. 4,659,774
U.S. Pat. No. 4,682,195
U.S. Pat. No. 4,683,202
U.S. Pat. No. 4,683,202
U.S. Pat. No. 4,684,611
U.S. Pat. No. 4,816,571
U.S. Pat. No. 4,879,236
U.S. Pat. No. 4,952,500
U.S. Pat. No. 4,959,463
U.S. Pat. No. 5,141,813
U.S. Pat. No. 5,264,566
U.S. Pat. No. 5,302,523
U.S. Pat. No. 5,322,783
U.S. Pat. No. 5,384,253
U.S. Pat. No. 5,428,148
U.S. Pat. No. 5,464,765
U.S. Pat. No. 5,538,877
U.S. Pat. No. 5,538,880
U.S. Pat. No. 5,550,318
U.S. Pat. No. 5,554,744
U.S. Pat. No. 5,563,055
U.S. Pat. No. 5,574,146
U.S. Pat. No. 5,580,859
U.S. Pat. No. 5,589,466
U.S. Pat. No. 5,602,244
U.S. Pat. No. 5,610,042
U.S. Pat. No. 5,645,897
U.S. Pat. No. 5,656,610
U.S. Pat. No. 5,702,932
U.S. Pat. No. 5,705,629
U.S. Pat. No. 5,736,524
U.S. Pat. No. 5,780,448
U.S. Pat. No. 5,789,215
U.S. Pat. No. 5,871,986
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624
Almendro et al., *J. Immunol.*, 157(12):5411-5421, 1996.
Angel et al., *Cell*, 49:729, 1987b.
Angel et al., *Mol. Cell. Biol.*, 7:2256, 1987a.

Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1996.
Baculovirus Expression Vectors, A Laboratory Manual, and Current Protocols in Molecular Biology, Bio/Technology, 6, 47, 1988.
Baculovirus Expression Vectors, A Laboratory Manual, W. H. Freeman and Company, New York, 1992.
Banerji et al., *Cell*, 27(2 Pt 1):299-308, 1981.
Banerji et al., *Cell*, 33(3):729-740, 1983.
Bates, *Mol. Biotechnol.*, 2(2):135-145, 1994.
Battraw and Hall, *Theor. App. Genet.*, 82(2):161-168, 1991.
Berkhout et al., *Cell*, 59:273-282, 1989.
Bhattacharjee et al., *J. Plant Bioch. Biotech.*, 6(2):69-73. 1997.
Blanar et al., *EMBO J*, 8:1139, 1989.
Bodine and Ley, *EMBO J*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Bulla and Siddiqui, *J. Virol.*, 62:1437, 1986.
Campbell and Villarreal, *Mol. Cell. Biol.*, 8:1993, 1988.
Campbell et al., *Proc. Natl. Acad. Sci. USA*, 99(12), 2002.
Campere and Tilghman, *Genes and Dev.*, 3:537, 1989.
Campo et al., *Nature*, 303:77, 1983.
Capaldi et al., *Biochem. Biophys. Res. Comm.*, 74(2):425-433, 1977.
Carbonelli et al., *FEMS Microbiol. Lett.*, 177(1):75-82, 1999.
Celander and Haseltine, *J. Virology*, 61:269, 1987.
Celander et al., *J. Virology*, 62:1314, 1988.
Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7(8):2745-2752, 1987.
Chiu et al., *Nat. Cell. Biol,*. 4(5):343-350, 2002.
Choi et al., *Cell*, 53:519, 1988.
Christou et al., *Proc. Natl. Acad. Sci. USA*, 84(12):3962-3966, 1987.
Clegg, *Methods Enzymol.*, 211:353-388, 1992.
Cocea, *Biotechniques*, 23(5):814-816, 1997.
Cohen et al., *J. Cell. Physiol.*, 5:75, 1987.
Costa et al., *Mol. Cell. Biol.*, 8:81, 1988.
Cripe et al, *EMBO J.*, 6:3745, 1987.
Cubitt et al., *Methods Cell Biol.*, 58:19-30, 1999.
Culotta and Hamer, *Mol. Cell. Biol.*, 9:1376, 1989.
Dandolo et al., *J. Virology*, 47:55-64, 1983.
De Villiers et al., *Nature*, 312(5991):242-246, 1984.
Deschamps et al., *Science*, 230:1174-1177, 1985.
D'Halluin et al., *Plant Cell*, 4(12):1495-1505, 1992.
Edbrooke et al., *Mol. Cell. Biol.*, 9:1908, 1989.
Edlund et al., *Science*, 230:912-916, 1985.
EPO 0273085
Fechheimer et al., *Proc. Natl. Acad. Sci. USA*, 84:8463-8467, 1987.
Feng and Holland, *Nature*, 334:6178, 1988.
Firak and Subramanian, *Mol. Cell. Biol.*, 6:3667, 1986.
Foecking and Hofstetter, *Gene*, 45(1):101-105, 1986.
Forster, V., *Ann. Phys.*, 6:54, 1948.
Fraley et al., *Proc. Natl. Acad. Sci. USA*, 76:3348-3352, 1979.
Froehler et al., *Nucleic Acids Res.*, 14(13):5399-5407, 1986.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gilles et al., *Cell*, 33:717, 1983.
Gloss et al., *EMBO J.*, 6:3735, 1987.
Godbout et al., *Mol. Cell. Biol.*, 8:1169, 1988.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Graham and Van Der Eb, *Virology*, 52:456-467, 1973.
Greene et al., *Immunology Today*, 10:272, 1989
Griesbeck et al., *J. Biol. Chem.*, 276(31):29188-29194, 2001.
Griesbeck et al., *J. Biol. Chem.*, 276:29188-29194, 2001.
Grosschedl and Baltimore, *Cell*, 41:885, 1985.
Harlan and Weintraub, *J. Cell Biol.*, 101:1094-1099, 1985.
Haslinger and Karin, *Proc. Natl. Acad. Sci. USA*, 82:8572, 1985.
Hauber and Cullen, *J. Virology*, 62:673, 1988.
He et al., *Plant Cell Reports*, 14 (2-3):192-196, 1994.
Heim and Tsien, *Curr. Biol.*, 6(2):178-182, 1996.
Heim and Tsien, *Curr. Biol.*, 6:178-182, 1996.
Heim et al., *Proc. Natl. Acad. Sci. USA*, 91(26):12501-1254, 1994.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Hong et al., *FEBS Lett.*, 400(2):233-237, 1997.
Horlick and Benfield, *Mol. Cell. Biol.*, 9:2396, 1989.
Hou and Lin, *Plant Physiology*, 111:166, 1996.
Huang et al., *Cell*, 27:245, 1981.
Hug et al., *Mol. Cell. Biol.*, 8:3065, 1988.
Hwang et al., *Mol. Cell. Biol.*, 10:585, 1990.
Hyun Bae et al., *J. Mol. Biol.*, 328:1071-1081, 2003.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Inouye and Inouye, *Nucleic Acids Res.*, 13: 3101-3109, 1985.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Kadesch and Berg, *Mol. Cell. Biol.*, 6:2593, 1986.
Kaeppler et al., *Plant Cell Reports*, 9:415-418, 1990.
Kaneda et al., *Science*, 243:375-378, 1989.
Karin et al., *Mol. Cell. Biol.*, 7:606, 1987.
Katinka et al., *Cell*, 20:393, 1980.
Kato et al, *J. Biol. Chem.*, 266:3361-3364, 1991.
Kawamoto et al., *Mol. Cell. Biol.*, 8:267, 1988.
Kiledjian et al., *Mol. Cell. Biol.*, 8:145, 1988.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Krieglar et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.

Lareyre et al., *J. Biol. Chem.*, 274(12):8282-8290, 1999.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lazzeri, *Methods Mol Biol*, 49:95-106, 1995.
Lee et al., *Biochem. Biophys. Res. Commun.*, 240(2):309-313, 1997.
Lee et al., *Environ. Mol. Mutagen.*, 13(1):54-59, 1989.
Lee et al., *Nature*, 294:228, 1981.
Lee et al., *Nucleic Acids Res.*, 12:4191-206, 1984.
Levenson et al., *Hum. Gene Ther.*, 9(8):1233-1236, 1998.
Levinson et al., *Nature*, 295:79, 1982.
Lin et al., *Mol. Cell. Biol.*, 10:850, 1990.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Majors and Varmus, *Proc. Natl. Acad. Sci. USA*, 80:5866, 1983.
Maniatis, et al., Molecular Cloning, A Laboratory Manual, Cold Spring Harbor Press, Cold Spring Harbor, N.Y., 1990.
McNeall et al., *Gene*, 76:81, 1989.
Miksicek et al., *Cell*, 46:203, 1986.
Miyawaki et al., *Nature*, 388:882-887, 1997.
Mordacq and Linzer, *Genes and Dev.*, 3:760, 1989.
Moreau et al., *Nucl. Acids Res.*, 9:6047, 1981.
Muesing et al., *Cell*, 48:691, 1987.
Nabel et al., *Science*, 244(4910):1342-1344, 1989.
Nagai et al., *Nat. Biotechnol.*, 20(1):87-90, 2002.
Nagai et al., *Nat. Biotechnol.*, 20:87-90, 2002.
Ng et al., *Nuc. Acids Res.*, 17:601, 1989.
Nicolau and Sene, *Biochim. Biophys. Acta*, 721:185-190, 1982.
Nicolau et al., *Methods Enzymol.*, 149:157-176, 1987.
Nomoto et al., *Gene*, 236(2):259-271, 1999.
Omirulleh et al., *Plant Mol. Biol.*, 21(3):415-28, 1993.
Ondek et al., *EMBO J.*, 6:1017, 1987.
Ormo et al., *Science*, 273(5280):1392-1395, 1996.
Ormo et al., *Science*, 273:1392-1395, 1996.
Omitz et al., *Mol. Cell. Biol.*, 7:3466, 1987.
Palmiter et al., *Nature*, 300:611, 1982.
Patterson et al., *Anal. Biochem.*, 10:284, 2000.
Patterson et al., *Anal. Biochem.*, 284(2):438-440, 2000.
Patterson et al., *Anal. Biochem.*, 284:438-440, 2000.
Patterson et al., *J. Cell Sci.*, 114:837-838, 2001.
PCT Appln. WO 9217598
PCT Appln. WO 94/09699
PCT Appln. WO 94/09699
PCT Appln. WO 95/06128
Pech et al., *Mol. Cell. Biol.*, 9:396, 1989.
Pelletier and Sonenberg, *Nature*, 334(6180):320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199:183-188, 1985.
Potter et al., *Proc. Natl. Acad. Sci. USA*, 81:7161-7165, 1984.
Prasher et al., *Gene*, 111:229-233, 1992.
Queen and Baltimore, *Cell*, 35:741, 1983.
Quinn et al., *Mol. Cell. Biol.*, 9:4713, 1989.
Reddy et al., 9(22):1542-1550, 2002.
Redondo et al., *Science*, 247:1225, 1990.
Reid et al., *Biochemistry*, 36:6786-6791, 1997.
Reisman and Rotter, *Mol. Cell. Biol.*, 9:3571, 1989.
Resendez Jr. et al., *Mol. Cell. Biol.*, 8:4579, 1988.
Rhodes et al., *Methods Mol. Biol.*, 55:121-131, 1995.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Rizzo et al., *J. Biol. Chem.*, 277:34168-34175, 2002.
Rizzo et al., *Nat. Biotechnol.*, 22(4):445-449, 2004.
Rosen et al., *Cell*, 41:813, 1988.
Sakai et al., *Genes and Dev.*, 2:1144, 1988.
Sambrook et al., In: *Molecular cloning*, Cold Spring Harbor Laboratory Press, Cold Spring Harbor, NY, 2001.
Satake et al., *J. Virology*, 62:970, 1988.
Schaffner et al., *J. Mol. Biol.*, 201:81, 1988.
Searle et al., *Mol. Cell. Biol.*, 5:1480, 1985.
Sekar and Periasamy, *J. Cell. Biol.*, 160:629-633, 2003.
Shagin et al., *Mol. Biol. Evol.*, 21(5):841-850, 2004.
Sharp and Marciniak, *Cell*, 59:229, 1989.
Shaul and Ben-Levy, *EMBO J*, 6:1913, 1987.
Sherman et al., *Mol. Cell. Biol.*, 9:50, 1989.
Sleigh and Lockett, *J EMBO*, 4:3831, 1985.
Spalholz et al., *Cell*, 42:183, 1985.
Spandau and Lee, *J. Virology*, 62:427, 1988.
Spandidos and Wilkie, *EMBO J*, 2:1193, 1983.
Stephens and Hentschel, *Biochem. J*, 248:1, 1987.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Swedlow et al., *Proc. Natl. Acad. Sci. USA*, 99:2014-2019, 2002.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Thiesen et al., *J. Virology*, 62:614, 1988.
Ting et al., *Proc. Natl. Acad. Sci. USA*, 98:15003-15008, 2001.
Treisman, *Cell*, 42:889, 1985.
Tronche et al., *Mol. Biol. Med.*, 7:173, 1990.
Trudel and Constantini, *Genes and Dev.* 6:954, 1987.
Truong et al., *Nat. Struct. Biol.*, 8:1069-1073, 2001.
Tsien, *Ann. Rev. Biochem.*, 67:509-544, 1998.
Tsukada et al., *Plant Cell Physiol.*, 30(4)599-604, 1989.
Tsumaki et al., *J. Biol. Chem.*, 273(36):22861-22864, 1998.
Tur-Kaspa et al., *Mol. Cell Biol.*, 6:716-718, 1986.
Tyndell et al., *Nuc. Acids. Res.*, 9:6231, 1981.
Vanderklish et al., *Proc. Natl. Acad. Sci. USA*, 97:2253-2258, 2000.
Vannice and Levinson, *J. Virology*, 62:1305, 1988.
Vasseur et al., *Proc Natl. Acad. Sci. U.S.A.*, 77:1068, 1980.
Wagner et al., *Proc. Natl. Acad. Sci. USA* 87(9):3410-3414, 1990.
Wang and Calame, *Cell*, 47:241, 1986.
Weber et al., *Cell*, 36:983, 1984.
Weinberger et al. *Mol. Cell. Biol.*, 8:988, 1984.
Wilson et al., *Science*, 244:1344-1346, 1989.
Winoto and Baltimore, *Cell* 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.

Wu et al., *Biochem. Biophys. Res. Commun.*, 233(1):221-6, 1997.
Yang et al., *Proc. Natl. Acad. Sci. USA*, 87:9568-9572, 1990.
Yutzey et al. *Mol. Cell. Biol.*, 9:1397, 1989.
Zacharias et al., *Science*, 296(5569):913-916, 2002.
Zacharias et al., *Science*, 296:913-916, 2002.
Zhang et al., *Nat. Rev. Mol. Cell Biol.*, 3:906-918, 2002.
Zhang et al., *Proc. Natl. Acad. Sci. USA*, 98:14997-15002, 2001.
Zhao-Emonet et al., *Biochim. Biophys. Acta*, 1442(2-3):109-119, 1998.
Zhou et al., *Exp. Hematol*, 21:928-933, 1993.

What is claimed is:

1. A nucleic acid encoding a modified fluorescent protein, wherein said modified fluorescent protein comprises the sequence of SEQ ID NO: 58, with the following modifications: an amino acid other than Y at position 145, a substitution of phenylalanine at position 64 with leucine, a substitution of serine at position 65 with threonine, a substitution of tyrosine at position 66 with tryptophan, a substitution of asparagine at position 146 with isoleucine, a substitution of methionine at position 153 with threonine, a substitution of valine at position 163 with alanine, a substitution of histidine at position 231 with leucine, and an addition of valine between positions 1 and 2.

2. The nucleic acid of claim 1, wherein the modification at position 145 of the modified fluorescent protein is selected from the group consisting of an alanine (Y145A), histidine (Y145H), proline (Y145P), and glycine (Y145G).

3. The nucleic acid of claim 2, wherein said modified fluorescent protein further comprises a modification at position 148.

4. The nucleic acid of claim 3, wherein said modified fluorescent protein comprises at position 148 a glutamic acid (H148E) or aspartic acid (H148D).

5. The nucleic acid of claim 4, wherein said modified fluorescent protein comprises Y145A/H148D.

6. An isolated host cell comprising nucleic acid encoding a modified fluorescent protein, wherein said "modified fluorescent protein comprises the sequence of SEQ ID NO: 58, with the following modifications: an amino acid other than Y at position 145, a substitution of phenylalanine at position 64 with leucine, a substitution of serine at position 65 with threonine, a substitution of tyrosine at position 66 with tryptophan, a substitution of asparagine at position 146 with isoleucine, a substitution of methionine at position 153 with threonine, a substitution of valine at position 163 with alanine, a substitution of histidine at position 231 with leucine, and an addition of valine between positions 1 and 2.

7. The host cell of claim 6, wherein the modification at position 145 of the modified fluorescent protein is selected from the group consisting of an alanine (Y145A), histidine (Y145H), proline (Y145P), and glycine (Y145G).

8. The host cell of claim 6, wherein said modified fluorescent protein further comprises a modification at position 148.

9. The host cell of claim 8, wherein said modified fluorescent protein comprises at position 148 a glutamic acid (H148E) or aspartic acid (H148D).

10. The host cell of claim 9, wherein said modified fluorescent protein comprises Y145A/H148D.

11. The nucleic acid of claim 1, wherein said modified fluorescent protein further comprises at position 72 an alanine (S72A).

12. The host cell of claim 6, wherein said modified fluorescent protein further comprises at position 72 an alanine (S72A).

* * * * *

SEQUENCE LISTING

```
<160> NUMBER OF SEQ ID NOS: 57

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
gagcacccag tccaaactga gcaaagacc                                         29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
ggtctttgct cagtttggac tgggtgctc                                         29

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
cttcggctac ggcctgatgt gcttcgcccg ctacc                                  35

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ggtagcgggc gaagcacatc aggccgtagc cgaag                                  35

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ggtgagaatc caagctaggt tggcgagatt ttcagg                                 36
```

```
<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
cctgaaaatc tcgccaacct agcttggatt ctcacc                               36

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ccatcaccat cacgggctag ccgacctgca gcc                                  33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ggctgcaggt cggctagccc gtgatggtga tgg                                  33

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
gctagccgac ctgcggccgc gcttaattag ctgagc                               36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gctcagctaa ttaagcgcgg ccgcaggtcg gctagc                               36

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Ser Gly Leu Arg Ser Arg Ala Gln Ala Ser Asn Ser Ala Val Asp Gly
 1               5                  10                  15

Thr Ala Gly Pro Gly Ser Pro Pro Val Ala Thr
```

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 12
gcagtgcttc gcccgctacc c                                         21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 13
gggtagcggg cgaagcactg c                                         21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic Primer

<400> SEQUENCE: 14
ggagtacaac gacatcagcc ac                                        22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic Primer

<400> SEQUENCE: 15
gtggctgatg tcgttgtact cc                                        22

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic Primer

<400> SEQUENCE: 16
aactacatca gcgacaacgt ctata                                     25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic Primer

<400> SEQUENCE: 17
tatagacgtt gtcgctgatg tagtt                                     25

-continued

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (11)..(12)
<223> OTHER INFORMATION: N = A, C, G, OR T/U

<400> SEQUENCE: 18
ggagtacaac nncatcagcg ac                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (11)..(12)
<223> OTHER INFORMATION: N = A, C, G OR T/U

<400> SEQUENCE: 19
gtcgctgatg nngttgtact cc                                              22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
ggagtacaac gccatcagcg ac                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
gtcgctgatg gcgttgtact cc                                              22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
aaggatcccc accggtcgcc                                                 20

<210> SEQ ID NO 23
<211> LENGTH: 23
<212> TYPE: DNA
<213> ORGANISM: Artificial Sequence -continued

```
<220> FEATURE:
<223> OTHER INFORMATION: Description of Artificial Sequence: Synthetic
      Primer

<400> SEQUENCE: 23
ttgagctcga gatctgagtc cgg                                               23

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
ctgagcaccc agtccaaact gagcaaagac ccc                                    33

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ggggtctttg ctcagtttgg actgggtgct cag                                    33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
ctgagctacc agtccaaact gagcaaagac ccc                                    33

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
ggggtctttg ctcagtttgg actggtagct cag                                    33

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
gcacccagtc caagctgagc aaaga                                             25

<210> SEQ ID NO 29
<211> LENGTH: 25
<212> TYPE: DNA
<213> ORGANISM: Artificial Sequence
<220> FEATURE:
```

<223> OTHER INFORMATION: Description of Artificial Sequence: Synthetic
      Primer

<400> SEQUENCE: 29
tctttgctca gcttggactg ggtgc                                         25

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
ctgagctacc agtccaaact gagcaaagac ccc                                33

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
ggggtctttg ctcagtttgg actggtagct cag                                33

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
tttaccggtc gccaccatgg tgag                                          24

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
ttcttacttg tacagctcgt ccatgccg                                      28

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
tttagtgaac cgtcagatcc gc                                            22

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 35
aatccggagg cgaaggcg                                                 18

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
tggcagcgtc tacaatcgcg                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
acgcgattgt agacgctgcc                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
cccactgcct ctacatctgg                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
ccagatgtag aggcagtggg                                               20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
ccttcaagat ttgccacgag                                               20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 41
ctcgtggcaa atcttgaagg                                              20

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
tatgagcctg acggagaccg tgc                                          23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
gcacggtctc cgtcaggctc ata                                          23

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
ccacgagatc gccggcagca a                                            21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
ttgctgccgg cgatctcgtg g                                            21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
gatggagggc gatgtggatg g                                            21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
```

<400> SEQUENCE: 47
ccatccacat cgccctccat c                                          21

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
aaagctagcg ctaccggtcg ccacc                                      25

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49
ttttccggac aggtaggtct tgc                                        23

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50
aaggatcccc accggtcgcc                                            20

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51
ttgagctcga gatctgagtc cgg                                        23

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 52
aaggatcccc accggtcgcc                                            20

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 53

```
aagaacatgt acaggtaggt cttgc                                          25

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 54
aaggatcccc accggtcgcc                                                20

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 55
ttcttgtaca tggcgaaggc gatg                                           24

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 56

Ser Gly Leu Arg Ser Pro Pro Val Ala Thr
 1               5                  10

<210> SEQ ID NO 57
<211> LENGTH: 44
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 57

Ser Gly Leu Arg Ser Arg Ala Gln Ala Ser Asn Ser Ala Val Asp Gly
 1               5                  10                  15

Thr Ala Gly Pro Gly Ser Arg Ala Gln Ala Ser Asn Ser Ala Val Asp
            20                  25                  30

Gly Thr Ala Gly Pro Gly Ser Pro Pro Val Ala Thr
        35                  40
```